United States Patent
Hof et al.

(10) Patent No.: US 9,879,300 B2
(45) Date of Patent: Jan. 30, 2018

(54) METHOD AND ARRAY FOR IDENTIFYING HISTONE-CODE-RELATED ANALYTES

(71) Applicant: UVic Industry Partnerships Inc., Victoria (CA)

(72) Inventors: Fraser Hof, Victoria (CA); Samuel Minaker, Victoria (CA); Kevin Daze, Victoria (CA); Sara Tabet, Victoria (CA); Manuel Ma, Victoria (CA)

(73) Assignee: UVic Industry Partnerships, Vancouver, British Columbia (CA)

( * ) Notice: Subject to any disclaimer, the term of this patent is extended or adjusted under 35 U.S.C. 154(b) by 620 days.

(21) Appl. No.: 14/302,238

(22) Filed: Jun. 11, 2014

(65) Prior Publication Data

US 2014/0357503 A1 Dec. 4, 2014

Related U.S. Application Data

(63) Continuation of application No. PCT/CA2012/001174, filed on Dec. 19, 2012.

(60) Provisional application No. 61/578,769, filed on Dec. 21, 2011.

(51) Int. Cl.

| | |
|---|---|
| *C12Q 1/25* | (2006.01) |
| *C07C 309/43* | (2006.01) |
| *C07C 309/44* | (2006.01) |
| *C07C 309/50* | (2006.01) |
| *C07C 309/60* | (2006.01) |
| *C12Q 1/00* | (2006.01) |
| *C40B 40/12* | (2006.01) |
| *C40B 40/04* | (2006.01) |
| *G01N 33/68* | (2006.01) |

(52) U.S. Cl.
CPC .............. *C12Q 1/25* (2013.01); *C07C 309/43* (2013.01); *C07C 309/44* (2013.01); *C07C 309/50* (2013.01); *C07C 309/60* (2013.01); *C12Q 1/00* (2013.01); *C40B 40/04* (2013.01); *C40B 40/12* (2013.01); *G01N 33/6803* (2013.01); *C07C 2603/92* (2017.05); *G01N 2440/00* (2013.01)

(58) Field of Classification Search
CPC . C07C 309/44; C07C 309/60; C07C 2103/92; G01N 2440/00
See application file for complete search history.

(56) References Cited

U.S. PATENT DOCUMENTS

| | | | | |
|---|---|---|---|---|
| 5,952,526 A | * | 9/1999 | Lamartine | C07C 303/02 562/74 |
| 2006/0019311 A1 | | 1/2006 | Moussa et al. | |
| 2010/0062540 A1 | * | 3/2010 | Cecillon | G01N 33/6896 436/501 |

FOREIGN PATENT DOCUMENTS

WO  WO 2013/091074  6/2013

OTHER PUBLICATIONS

Wikipedia, Aliphatic Compound, pp. 1-3, recovered from https://en.wikipedia.org/wiki/Aliphatic_compound Apr. 3, 2017.*
Heterocyclic Chemistry, Heterocyclic Compounds, recovered from https://www2.chemistry.msu.edu/faculty/reusch/virttxtjml/heterocy.htm on Apr. 3, 2017, pp. 1-14.*
Zaragoza Dorwald, Side Reactions in Organic Synthesis, 2005, WILEY-VCH Verlag GmbH & Co. KGaA, Weinheim, Preface. p. IX.*
Coleman et al., "Enhanced detection of the pathogenic prion protein by its supramolecular association with para-sulfonato-calix[n]arene derivatives," *New Journal of Chemistry* 31:711-717, 2007.
Lee et al., "Supramolecular fishing for plasma membrane proteins using an ultrastable synthetic host-guest binding pair," *Nature Chemistry* 3:154-159, 2011.
International Search Report from International Application No. PCT/CA2012/001174 dated Mar. 8, 2013.

* cited by examiner

*Primary Examiner* — Paul A Zucker
(74) *Attorney, Agent, or Firm* — Klarquist Sparkman, LLP

(57) ABSTRACT

Disclosed embodiments concern an array for use in identifying or identifying and quantifying analytes in a sample using a macrocyclic sensor comprising a macrocyclic compound and a detectable moiety. The disclosed array may be used to discriminate among various analytes based on different features, such as post-translational modifications, isomeric post-translational modifications, and the peptide sequence around post-translational modifications. Also disclosed is a method for identifying analytes comprising a post-translational modification, as well as an enzymatic assay using the disclosed macrocyclic sensor.

33 Claims, 18 Drawing Sheets

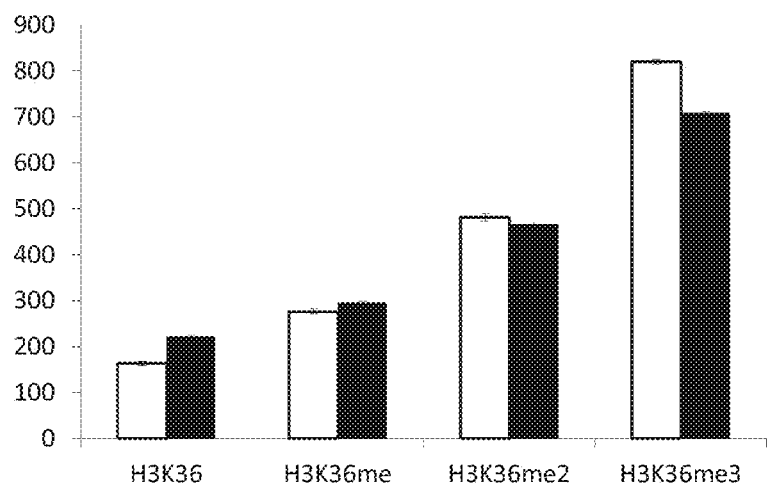
FIG. 12a
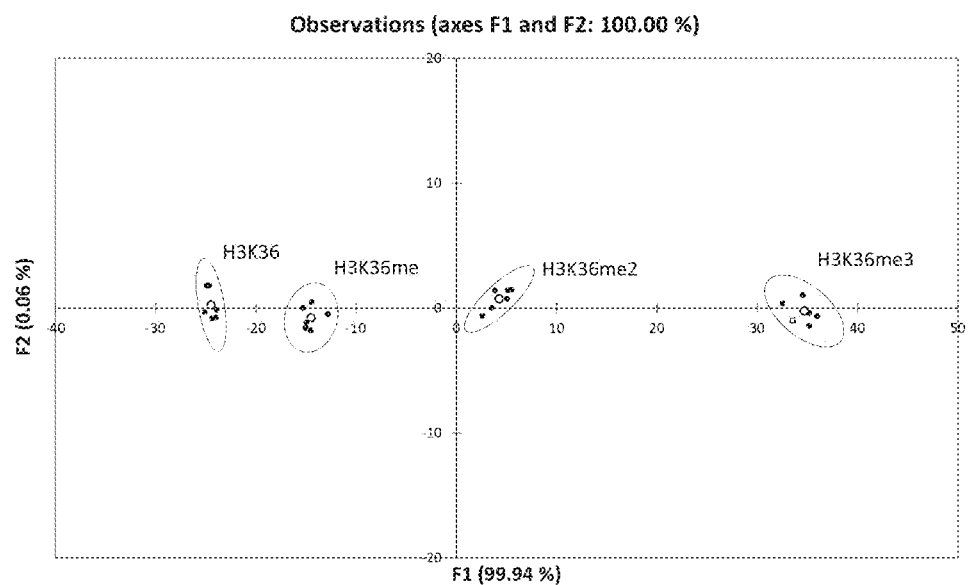
FIG 12.b

METHOD AND ARRAY FOR IDENTIFYING HISTONE-CODE-RELATED ANALYTES

CROSS REFERENCE TO RELATED APPLICATION

This application is a continuation of international application No. PCT/CA2012/001174, which claims the benefit of the earlier filing date of U.S. provisional patent application No. 61/578,769, filed Dec. 21, 2011, which prior applications are incorporated herein by reference in their entirety.

FIELD

Disclosed embodiments concern a macrocyclic sensor array and method for analyzing the post-translational modification state of analytes, particularly histone-code related analytes. The disclosed sensor array and method are useful in diagnostics and enzymatic assays.

BACKGROUND

Peptides and proteins in living organisms are frequently modified by additional chemical reactions that occur after their initial formation. These post-translational modifications (PTMs) include but are not limited to phosphorylation, acetylation, methylation, citrullination, crotonylation, butyrylation, ubiquitination, and Proline cis-trans isomerization. PTMs modulate the biological behaviors of the modified peptides and proteins and constitute an important family of biological control mechanisms. The enzymes that install and remove PTMs, as well as the modified peptides and proteins themselves, are frequently implicated as the causative agents of a wide variety of human diseases. PTMs of proteins involved in gene regulation and their associated enzymes are especially important in human cancer. Examples include the tumor suppressor protein p53, whose activities are controlled by lysine methylation and ubiquitination, as well as histones. Histones are proteins that bind to all DNA in the nucleus and create a condensed package of nucleic acids and their associated proteins called chromatin.

Histones are modified by various PTMs, most of which participate in signaling pathways that control the expression of the genes encoded in the associated DNA. The study of PTMs of histones in particular has led to the understanding that a core regulator of gene expression is a "histone code" that comprises multiple PTMs to the histones that are associated with a given DNA sequence. Gene (mis)regulation by epigenetic mechanisms is of critical importance in a large number of disease states, and the mechanisms are best understood in the area of cancer. The activities of various enzymes that install PTMs, enzymes that remove PTMs, and of the PTMs themselves are implicated as causative agents of cancer and are considered to be promising targets for new cancer therapies. Drugs that target histone acetylation (e.g. Vorinostat, a histone deacetylase inhibitor used clinically for the treatment of lymphoma) have already demonstrated that epigenetic gene regulation mechanisms are valid targets for cancer therapy.

Antibodies are the cornerstone of almost all efforts to "read the histone code," i.e. to analyze the post-translational states of epigenetic/histone targets for both diagnostic purposes and for use in enzyme assays. Antibodies can be raised against almost any peptide sequence, including one containing any specific post-translational modification of interest.

For applications broadly related to diagnostics, antibodies are the molecules used for identifying post-translationally modified peptides or proteins from complex mixtures (e.g. by use in western blots). For applications broadly related to enzyme assays, antibodies are the molecules used to identify and quantify products and/or starting materials in reaction mixtures after varying periods of time.

Despite their dominant position as biochemical tools, antibodies against histone PTM targets have several known shortcomings. Problems include high batch-to-batch variability, high costs, inherently poor selectivity between similar analytes (e.g. those bearing trimethyllysine at different positions on a single protein), and a high rate of failed specificity tests that has been documented to be as high as 25%. But the most serious problem that "quality control" can do little about is epitope masking—the mis-identification of analytes when an antibody misses its target residue because of the proximity of a neighboring residue that also bears a PTM. This problem is intrinsic to the antibody-based analysis of peptides and proteins that are densely decorated with PTMs, such as histones.

Varieties of assays for the enzymes that add and remove post-translational modifications exist and are used in drug discovery programs that search for therapeutic agents that modulate the enzymes' activities. Two broad varieties of assays are available: discontinuous assays that use a post-reaction treatment to identify and quantify the products of enzyme action; and continuous assays that rely on detection of by-products to report indirectly on the progress of the reaction.

One primary disadvantage of discontinuous assays is that they only provide information on the extent of reaction after a fixed amount of time has passed. They do not allow continuous observation of enzyme rate profiles that are more robust identifiers of inhibitors. Homogeneous variants that rely on antibodies have also been developed, but still suffer from the fact that they are operated in a discontinuous manner.

Continuous assays in this field are many and varied in the biochemical mechanisms by which they report on reaction progress, but typically rely on detection of reaction by-products by coupling into subsequent reactions that produce an optical output. Examples can be chemically coupled to an optical output (such as assays that detect formaldehyde, the by-product of demethylase enzymes, by reaction with a chemical that generates a fluorescent product), or enzymatically coupled to produce an optical output (such as assays that detect S-adenosyl homocysteine, the by-product of all methyltransferases, by inclusion of one or more other enzymes that convert it into a chemical species that produces an optical signal).

There is growing appreciation that the specific methylation states of products and starting materials are highly relevant to drug discovery. For example, one highly oncogenic protein can add methyl groups to H3K27me2, but not H3K27me1 or H3K27me0. The drug target demethylase LSD1 specifically removes methyl groups from p53K370me2 to make p53K370me0 (which inactivates p53 and is oncogenic) but is less active against K370me1 (which has distinct biological function) in vivo. LSD1 also demethylates H3K4me2, but not H3K4me3, to generate oncogenic H3K4me0, but has been reported to act instead on H3K9me2 to produce H3K9me0 in the presence of certain cofactors.

There exists a need in the art for an assay that can report in a continuous, homogeneous manner on both the progression of these enzymes' reactions and the identity of the products. There also exists a need for a method of identifying and characterizing analytes comprising post-translational modifications, such as histones, using antibody-free techniques.

SUMMARY

The present disclosure concerns a macrocyclic compound having a formula

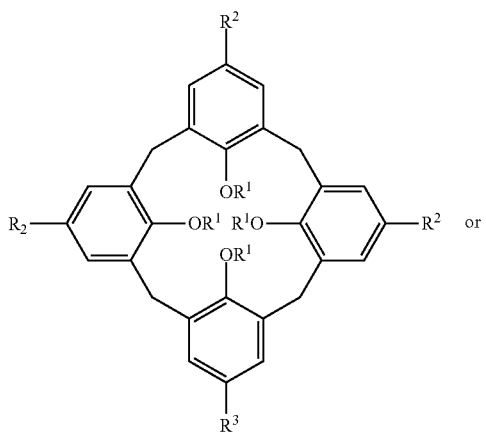

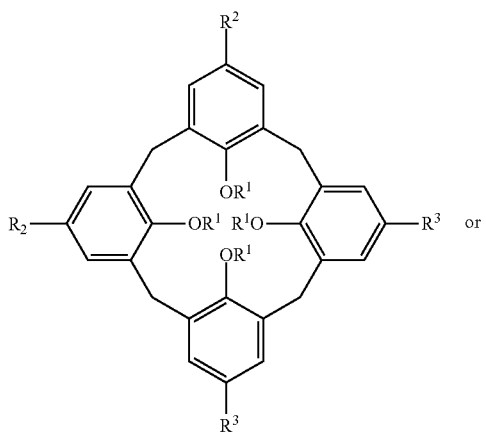

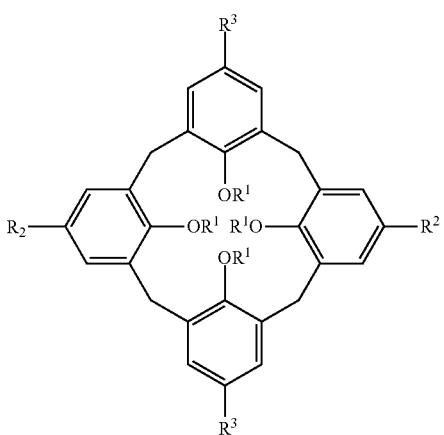

wherein $R^1$ is selected from H or aliphatic, $R^2$ is selected from $SO_3H$, $CO_2H$, and $PO_3H_2$, and $R^3$ is selected from halogen, heteroaryl, aryl, heteroaliphatic, and combinations thereof. In particular disclosed embodiments, $R^1$ may be selected from $(CH_2)_mCH_3$ where m is 0, 1, 2, 3, 4, 5, 6, or 7, or a branched or straight-chain $C_1$-$C_8$-alkyl or $C_1$-$C_8$ alkenyl; and $R^3$ is selected from F, Cl, Br, I, $NH_2$, $NHR^a$, $NR^aR^b$, $(NR^aR^bR^c)^+$, wherein $R^a$, $R^b$ and $R^c$ independently are selected from methyl, ethyl, propyl, aryl, or $(CH_2)_m$-alkyl where m=0, 1, or 2 and alkyl is branched, straight-chain, cyclic $C_1$-$C_8$-alkyl, $C_1$-$C_8$ alkenyl, or —$SO_2$aryl wherein the aryl group is optionally substituted with one or more functional groups selected from cyano, amide, carboxyl, carboxylic acid, amine, alkyl amine, $C_1$-$C_{10}$alkyl, $C_1$-$C_{10}$alkoxy, halo, aldehyde, hydroxyl, $C_1$-$C_{10}$alkylhydroxyl, and combinations thereof. In particular disclosed embodiments, $R^3$ may be optionally substituted with one or more functional groups selected from cyano, amide, carboxyl, carboxylic acid, amine, alkyl amine, $C_1$-$C_{10}$alkyl, $C_1$-$C_{10}$alkoxy, halo, aldehyde, hydroxyl, $C_1$-$C_{10}$alkylhydroxyl, and combinations thereof.

Also disclosed herein is an array, comprising at least two macrocyclic sensors wherein the at least two different macrocyclic sensors are capable of identifying or identifying and quantifying an analyte having at least one post-translational modification. Typically, the at least two macrocyclic sensors are not the same and each comprises a macrocyclic compound and a detectable moiety. In particular disclosed embodiments, the macrocyclic compound is a single cyclic or multi-cyclic compound having one or more rings with the total number of atoms in each ring ranging from about 3 to about 100, more typically from about 3 to about 75, even more typically from about 3 to about 50. A macrocycle comprising multiple rings may further comprise a spacer, such as an aliphatic or heteroaliphatic chain ranging from 1 to about 10 carbon atoms, heteroatoms, or combinations thereof, which separates the multiple rings from one another. In particular disclosed embodiments, the macrocyclic compound may be selected from calixarenes, cyclodextrins, cucurbiturils, and crown ethers.

In certain disclosed embodiments, the macrocyclic compound may have a formula selected from

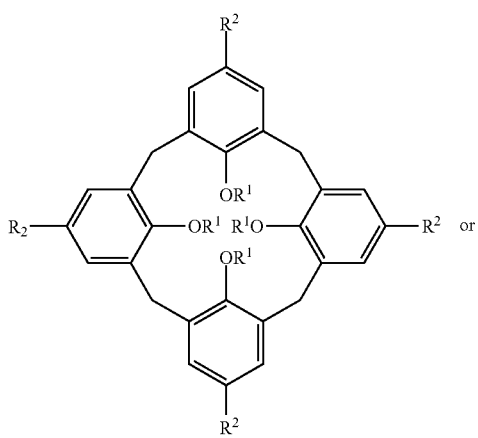

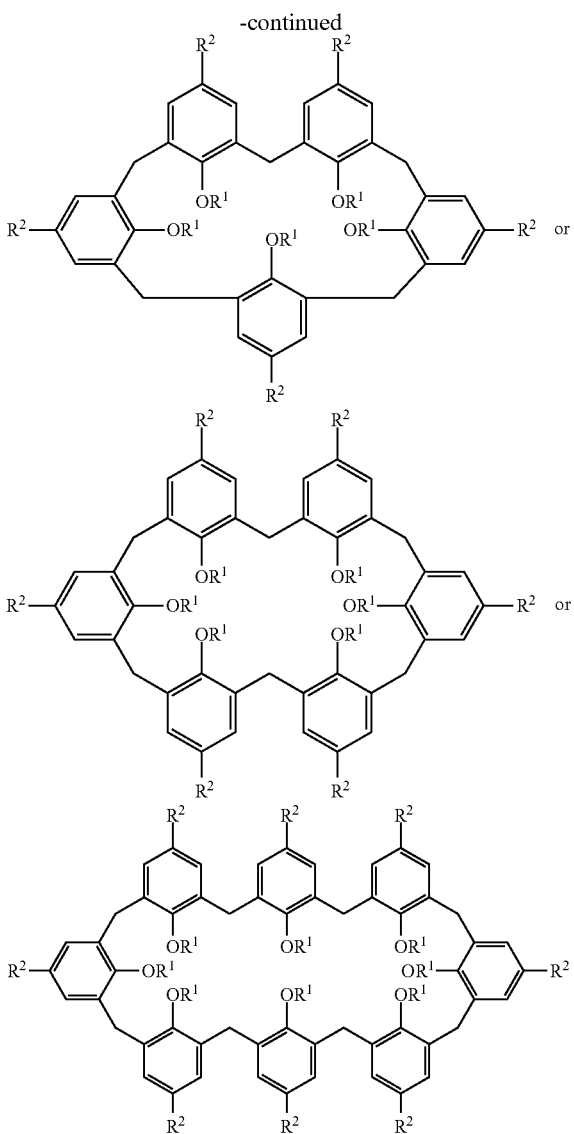

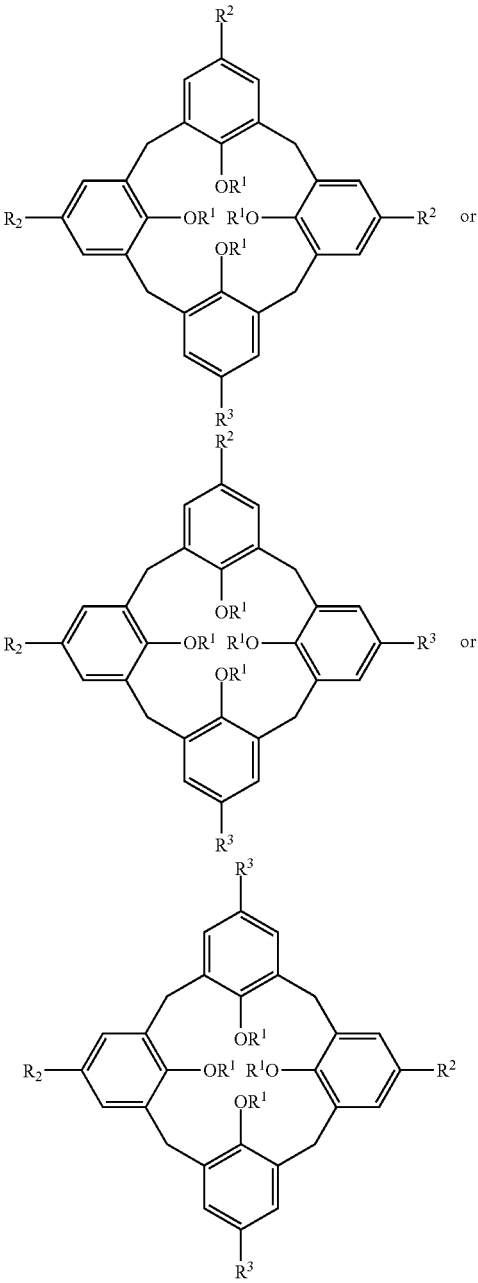

wherein R¹ is selected from H, aliphatic, such as alkyl, alkenyl, alkynyl; even more typically, R¹ may be selected from $(CH_2)_m CH_3$ where m is 0, 1, 2, 3, 4, 5, 6, or 7, or a branched or straight-chain $C_1$-$C_8$-alkyl or $C_1$-$C_8$ alkenyl. $R^2$ may be selected from aliphatic, aromatic, heteroaromatic, and heteroaliphatic. In particular disclosed embodiments, $R^2$ may be selected from alkyl, alkenyl, alkynyl, heteroalkyl, heteroalkenyl, and heteroalkynyl. In particular disclosed embodiments, $R^2$ is $(CH_2)_m X$ where m is 0, 1, 2 and X may be selected from F, Cl, Br, I, $SO_3H$, SH, COOH, $NH_2$, $NHR^a$, $NR^a R^b$, $(NR^a R^b R^c)^+$ wherein $R^a$, $R^b$ and $R^c$ independently are selected from aliphatic, particularly alkyl and lower alkyl (generally, $C_1$-$C_{10}$, such as methyl, ethyl, propyl), or aryl. In particular disclosed embodiments, the aliphatic or aryl group may be substituted with one or more functional groups selected from cyano, amide, carboxyl, carboxylic acid, amine, alkyl amine, alkyl (e.g., $C_1$-$C_{10}$alkyl, such as methyl, ethyl, propyl, butyl, etc.), alkoxy (e.g., $-OC_1$-$C_{10}$alkyl), halo (such as iodo, fluoro, chloro, or bromo), aldehyde, hydroxyl, alkylhydroxyl (e.g., $C_1$-$C_{10}$hydroxyl), and combinations thereof. In certain disclosed embodiment, $R^a$, $R^b$, and $R^c$ independently may be heteroaliphatic, such as —$SO_2$-phenyl wherein the phenyl group may be substituted with one or more functional groups selected from cyano, amide, carboxyl, carboxylic acid, amine, alkyl amine, alkyl (e.g., $C_1$-$C_{10}$alkyl, such as methyl, ethyl, propyl, butyl, etc.), alkoxy (e.g., —$OC_1$-$C_{10}$alkyl), halo (such as iodo, fluoro, chloro, or bromo), aldehyde, hydroxyl, alkylhydroxyl (e.g., $C_1$-$C_{10}$hydroxyl), and combinations thereof.

Other examples of macrocyclic compounds have any one of the following formulas:

wherein R¹ is selected from H, aliphatic, typically alkyl, alkenyl, or alkynyl. In particular disclosed embodiments, R¹ is $(CH_2)_m CH_3$ where m is 0, 1, 2, 3, 4, 5, 6, or 7, or a branched or straight-chain $C_1$-$C_8$-alkyl or $C_1$-$C_8$ alkenyl; $R^2$ is selected from $SO_3H$, $CO_2H$, and $PO_3H_2$; $R^3$ is selected from halogen (such as F, Cl, Br, I), aryl, heteroaryl, and heteroaliphatic. In particular disclosed embodiments, $R^3$ may be selected from $NH_2$, $NHR^a$, $NR^aR^b$, $(NR^aR^bR^c)^+$, wherein $R^a$, $R^b$ and $R^c$ independently are selected from aliphatic, such as alkyl, alkenyl, alkynyl; even more typically methyl, ethyl, propyl, aryl, or $(CH_2)_m$-alkyl where m=0, 1, or 2 and alkyl is branched, straight-chain, cyclic $C_1$-$C_8$-alkyl, or $C_1$-$C_8$ alkenyl. In particular disclosed embodiments, $R^3$ may be selected from aryl, heteroaryl, and heteroaliphatic optionally substituted with one or more functional groups selected from cyano, amide, carboxyl, carboxylic acid, amine, alkyl amine, alkyl (e.g., $C_1$-$C_{10}$alkyl, such as methyl, ethyl, propyl, butyl, etc.), alkoxy (e.g., —$OC_1$-$C_{10}$alkyl), halo (such as iodo, fluoro, chloro, or bromo), aldehyde, hydroxyl, alkylhydroxyl (e.g., $C_1$-$C_{10}$hydroxyl), and combinations thereof. In certain disclosed embodiments, $R^3$ may be —$SO_2$-phenyl wherein the phenyl group may be substituted with one or more functional groups selected from cyano, amide, carboxyl, carboxylic acid, amine, alkyl amine, alkyl (e.g., $C_1$-$C_{10}$alkyl, such as methyl, ethyl, propyl, butyl, etc.), alkoxy (e.g., —$OC_1$-$C_{10}$alkyl), halo (such as iodo, fluoro, chloro, or bromo), aldehyde, hydroxyl, alkylhydroxyl (e.g., $C_1$-$C_{10}$hydroxyl), and combinations thereof.

In particular disclosed embodiments, the macrocyclic compound may be a cyclodextrin having any one of the following formulas

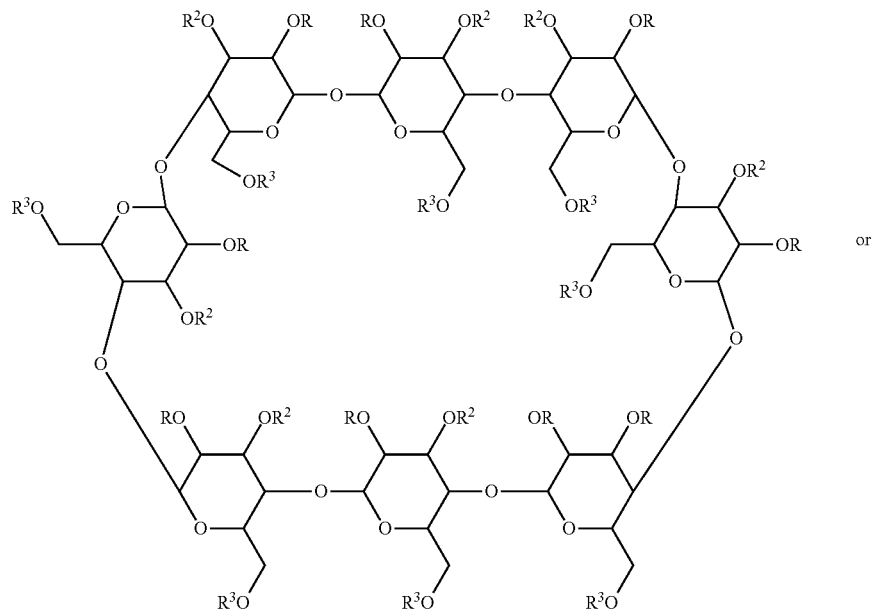

or

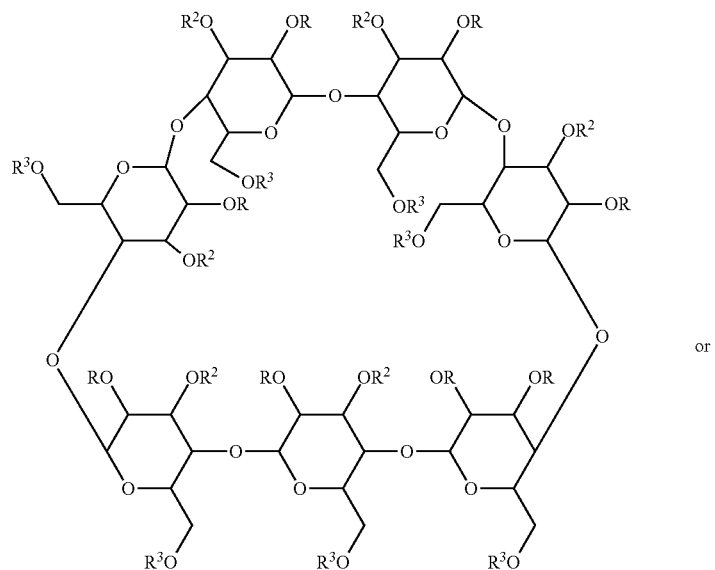

or

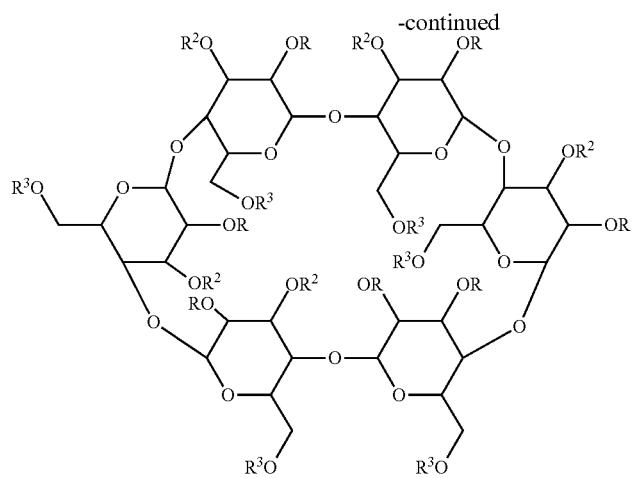

wherein each R, $R^2$, $R^3$ is selected from H, aliphatic, such as alkyl, alkenyl, and alkynyl, heteroaliphatic, such as heteroalkyl, heteroalkenyl, and heteroalkynyl, and aryl; particularly methyl, ethyl, n-propyl, i-propyl, butyl, octyl, $(CH_2)_{1,2}COOH$, $(CH_2)_{2,3}OH$, acetyl, benzoyl, sulpho, succinyl; $OR^3$ is replaced with any one of $NH_2$, $NHR^a$, $NR^aR^b$, $(NR^aR^bR^c)^+$, wherein $R^a$, $R^b$ and $R^c$ independently are selected from aliphatic, such as alkyl, alkenyl, alkynyl; even more typically methyl, ethyl, n-propyl, i-propyl; aryl; and heteroaliphatic; more typically $(CH_2)_{1,2}COOH$, $(CH_2)_{2,3}OH$, acetyl, benzoyl, sulpho, and succinyl.

Additionally, the macrocyclic compound may be a cucurbituril selected from the following

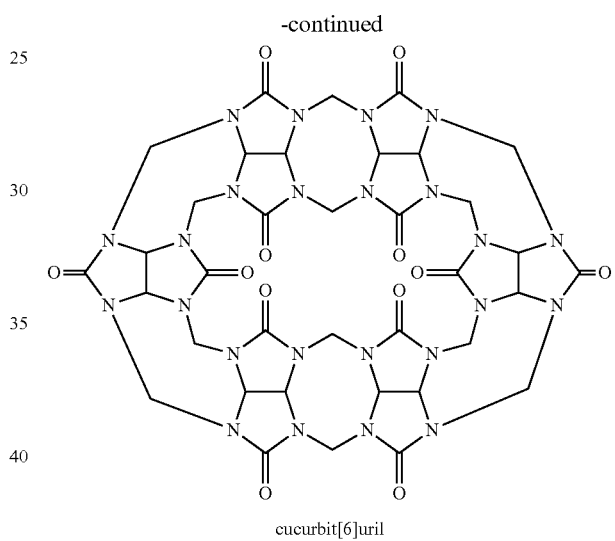

cucurbit[6]uril

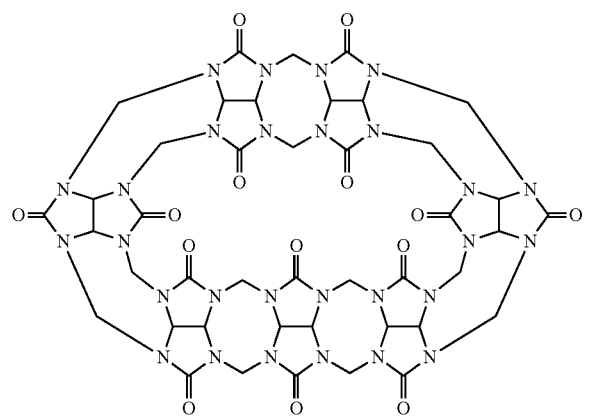

cucurbit[7]uril

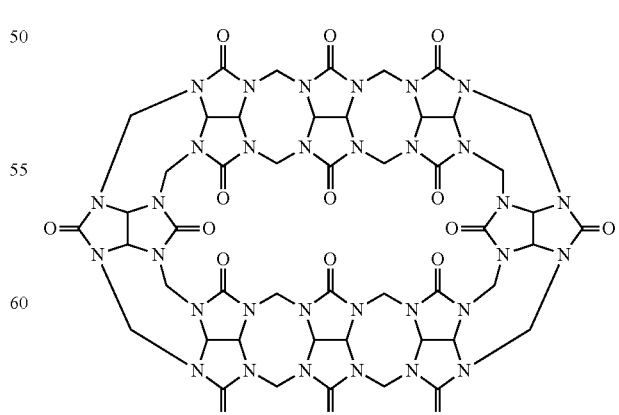

cucurbit[8]uril

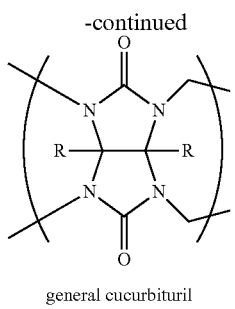

general cucurbituril

The disclosed macrocyclic sensor also comprises a detectable moiety, which may be any moiety capable of producing a signal, such as an optical signal. In particular disclosed embodiments, the optical signal may be produced by fluorescence and/or absorbance. Certain examples of detectable moities include dyes, such as members of the lucigenin family, the fluorescein family, the family of naphthalene-based dyes and/or pyrene-based dye, and the azole family. Exemplary dyes include, but are not limited to fluorescein, fluorescein isothiocyanate, rhodamine, tetramethyl rhodamine isothiocyanate (TRITC), naphthalimide, 4-dimethyl-aminonaphthalimide (4-DMN), coumarin, cyanine, dansyl, PSP, thiazole orange, Oregon green, eosin, Texas red, Cal Fluor, indocarbocyanine, oxacarbocyanine, thiacarbocyanine, merocyanine, Quasar dyes, prodan derivatives, pyridyloxazole, nitrobenzoxadiazole, benzoxadiazole, cascade blue, Nile red, Nile blue, cresyl violet, oxazine 170, proflavin, acridine orange, acridine yellow, auramine, crystal violet, malachite green, porphyrin, phtalocyanine, and bilirubin.

In the macrocyclic sensor, the macrocyclic compound is typically coupled with the detectable moiety. In particular disclosed embodiments, the macrocyclic compound is covalently coupled to the detectable moiety. In other disclosed embodiments, the macrocyclic compound is non-covalently coupled to the detectable moiety.

The disclosed macrocyclic sensor array may be used to identify an analyte. The analyte may be a biological molecule, such as an amino acid, a peptide, and a protein comprising at least one post-translational modification. Histones are exemplary proteins that may be detected and identified by the disclosed array. Examples of post-translational modification that may be detected include those that result from phosphorylation, methylation, acetylation, citrullination, butyrylation, crotonylation, ubiquitination, and proline cis-trans isomerization of the analyte.

The disclosed macrocyclic sensor array may be used for various different identification techniques. For example, the array may be used to identify members of a group of analytes comprising a single peptide or protein sequence bearing different post-translational modifications at a single site. Additionally, the array may be used to identify a particular peptide or protein sequence among a plurality of analytes that all comprise the same post-translational modification within different peptide or protein sequences. Another particular embodiment concerns identifying a product obtained by enzymatic post-translational modification of a peptide or protein. In particular disclosed embodiments, the analyte may be identified on the basis of an isomeric post-translational modification, degree of post translational modification, and a combination of different post-translational modifications.

Also disclosed is a method for identifying post-translational modifications, comprising providing a sample comprising at least one analyte having a post-translational modification, exposing the sample to at least two macrocyclic sensors, and detecting a signal produced by interaction between the at least one analyte and the at least two macrocyclic sensors. In particular disclosed embodiments, the sample may be exposed to at least two macrocyclic sensors by combining the sample with separate solutions wherein each separate solution comprises one of the at least two macrocyclic sensors. The signal that is produced using the disclosed method may be detected using any method now known or hereafter discovered to be capable of determining changes in fluorescence and/or absorbance by those having ordinary skill in the art. The signal may be produced when the at least one analyte displaces a detectable moiety that is non-covalently coupled with a macrocyclic compound. In other embodiments, the signal may be produced when the at least one analyte changes the environment of a detectable moiety covalently coupled with a macrocyclic compound through proximal effects sufficient to elicit a signal. The disclosed method may further comprise manipulating data obtained from detecting the signal using a chemometric method, such as principal component analysis, linear discriminant analysis, multilinear regressions, and neural network analyses.

Also disclosed is an enzymatic assay, comprising providing a sample comprising at least one analyte, exposing the sample to an enzyme, exposing the sample to a macrocyclic sensor, determining the progress of a reaction between the enzyme and the at least one analyte, and determining the identity of a product produced through the reaction between the enzyme and the at least one analyte. In addition, the disclosed enzymatic assay may be used to identify or identify and characterize compounds that inhibit enzymatic reactions, activate enzymatic reactions, and modulate one or more enzymes involved in an enzymatic reaction.

Also disclosed herein is a device for identifying or identifying and quantifying an analyte having a post-translational modification, comprising one or more well plates comprising a plurality of wells comprising at least two macrocyclic sensors according to any one of claims 3-15, a fluorometer or UV spectrometer, and a computer capable of receiving output from the fluorometer or UV spectrometer. Also disclosed herein is a computer readable medium containing computer-executable instructions for the method disclosed herein. A kit, comprising a macrocyclic sensor as disclosed herein is also described.

The foregoing and other objects, features, and advantages of the invention will become more apparent from the following detailed description, which proceeds with reference to the accompanying figures.

BRIEF DESCRIPTION OF THE DRAWINGS

FIG. 1a illustrates non-covalent binding of the detectable moiety to the macrocyclic compound and FIG. 1b illustrates covalent binding of the detectable moiety to the macrocyclic compound

FIG. 3a illustrates a fluorescein-labeled sensor and FIG. 3b illustrates a tetramethylrhodamine-labeled sensor.

FIG. 8a is a bar graph illustrating exemplary patterns of fluorescence data obtained in a particular embodiment of the disclosed array using embodiments of the disclosed sensor. FIG. 8b is a plot obtained using principal component analysis of replicated fluorescence data that illustrates the ability to differentiate analytes by pattern recognition.

FIG. 9a is a bar graph illustrating exemplary patterns of fluorescence data obtained in a particular embodiment. FIG. 9b is a plot obtained using linear discriminant analysis of replicated fluorescence data that illustrates the ability to differentiate analytes by pattern recognition.

FIGS. 12a and 12b collectively illustrate the ability of the disclosed array and sensors to discriminate closely related analytes on the basis of degree of post-translational methylation. FIG. 12a is a bar graph illustrating patterns of fluorescence data obtained in an exemplary embodiment. FIG. 12b is a plot obtained using linear discriminant analysis of replicated fluorescence data that illustrates the ability to differentiate analytes by pattern recognition.

FIG. 13a is a bar graph illustrating patterns of fluorescence data obtained in an exemplary embodiment. FIG. 13b is a plot obtained using linear discriminant analysis of replicated fluorescence data that illustrates the ability to differentiate analytes by pattern recognition.

FIG. 14a is a bar graph illustrating patterns of fluorescence data obtained in an exemplary embodiment. FIG. 14b is a plot obtained using linear discriminant analysis of replicated fluorescence data that illustrates the ability to differentiate analytes by pattern recognition.

FIG. 15a is a bar graph illustrating patterns of fluorescence data obtained in an exemplary embodiment. FIG. 15b is a plot obtained using principal component analysis of replicated fluorescence data that illustrates the ability to differentiate analytes by pattern recognition.

FIG. 16a comprises two graphs illustrating raw $F-F_0$ data for an exemplary embodiments of the disclosed sensor that track the conversion of one starting material into each of two possible products. FIG. 16b is a graph illustrating principal component analysis of the conversion data.

DETAILED DESCRIPTION

I. Definitions

Figure 1A:
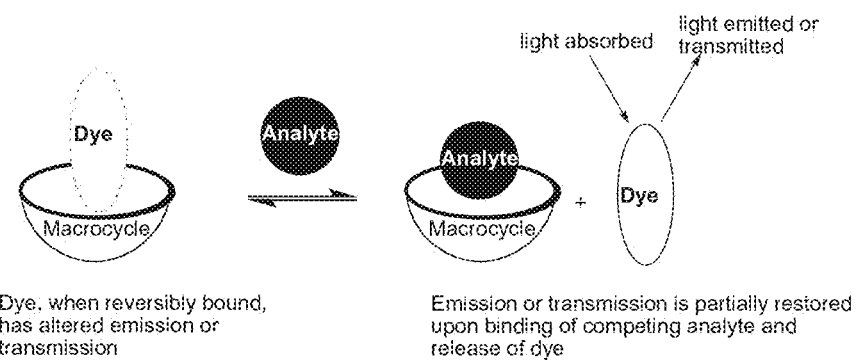
FIGS. 1a and 1b are schematic diagrams illustrating coupling of an analyte to embodiments of the disclosed sensor.

Unless otherwise noted, technical terms are used according to conventional usage. Definitions of common terms in molecular biology may be found in Benjamin Lewin, *Genes VII*, published by Oxford University Press, 2000 (ISBN 019879276X); Kendrew et al. (eds.), *The Encyclopedia of Molecular Biology*, published by Blackwell Publishers, 1994 (ISBN 0632021829); and Robert A. Meyers (ed.), *Molecular Biology and Biotechnology: a Comprehensive Desk Reference*, published by Wiley, John & Sons, Inc., 1995 (ISBN 0471186341); and other similar references.

As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B, or A and B. It is further to be understood that all nucleotide sizes or amino acid sizes, and all molecular weight or molecular mass values, given for nucleic acids or polypeptides or other compounds are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

In order to facilitate review of the various examples of this disclosure, the following explanations of specific terms are provided:

aDMA: asymmetric dimethylarginine

Aliphatic: Any open or closed chain molecule, excluding aromatic compounds, containing only carbon and hydrogen atoms in the chain, which are joined by single bonds (alkanes), double bonds (alkenes), or triple bonds (alkynes). This term encompasses substituted aliphatic compounds, saturated aliphatic compounds, and unsaturated aliphatic compounds.

Antibody: "Antibody" collectively refers to immunoglobulins or immunoglobulin-like molecules (including by way of example and without limitation, IgA, IgD, IgE, IgG and IgM, combinations thereof, and similar molecules produced during an immune response in any vertebrate, for example, in mammals such as humans, goats, rabbits and mice) and antibody fragments that specifically bind to a molecule of interest (or a group of highly similar molecules of interest) to the substantial exclusion of binding to other molecules (for example, antibodies and antibody fragments that have a binding constant, or binding affinity, for the molecule of interest that is at least $10^3$ $M^{-1}$ greater, at least $10^4$ M$^{-1}$ greater or at least $10^5$ M$^{-1}$ greater than a binding constant for other molecules in a biological sample. In one embodiment, binding affinity is calculated by a modification of the Scatchard method described by Frankel et al., *Mol. Immunol.*, 16:101-106, 1979. In another embodiment, binding affinity is measured by an antigen/antibody dissociation rate. In yet another embodiment, a high binding affinity is measured by a competition radioimmunoassay.

More particularly, "antibody" refers to a polypeptide ligand comprising at least a light chain or heavy chain immunoglobulin variable region which specifically recognizes and binds an epitope of an antigen. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody.

Antigen: A compound, composition, or substance that may be specifically bound by the products of specific humoral or cellular immunity, such as an antibody molecule or T-cell receptor. Antigens can be any type of molecule including, for example, haptens, simple intermediary metabolites, sugars (e.g., oligosaccharides), lipids, and hormones as well as macromolecules such as complex carbohydrates (e.g., polysaccharides), phospholipids, nucleic acids and proteins. Common categories of antigens include, but are not limited to, viral antigens, bacterial antigens, fungal antigens, protozoa and other parasitic antigens, tumor antigens, antigens involved in autoimmune disease, allergy and graft rejection, toxins, and other miscellaneous antigens. In one example, an antigen is a *Bacillus* antigen, such as γPGA.

Aromatic: A term describing conjugated rings having unsaturated bonds, lone pairs, or empty orbitals, which exhibit a stabilization stronger than would be expected by the stabilization of conjugation alone. It can also be considered a manifestation of cyclic delocalization and of resonance.

Aryl: A substantially hydrocarbon-based aromatic compound, or a radical thereof (e.g. $C_6H_5$) as a substituent bonded to another group, particularly other organic groups, having a ring structure as exemplified by benzene, naphthalene, phenanthrene, anthracene, etc. This term also encompasses substituted aryl compounds.

Coupled, Coupling, Couple: Associating or joining two components. In particular disclosed embodiments, coupling may encompass chemically linking two components together, such as through an ionic or covalent bond or through an electrostatic interaction. In particular disclosed embodiments, coupling may encompass associating two components together, such as through a non-covalent bond or chelation.

Detectable Moiety: A moiety capable of being detected, such as a moiety that absorbs or emits light so as to produce a signal. Examples of detectable moieties include dyes.

DCM: Dichloromethane.
DMF: Dimethylformamide.
DNA: Deoxyribonucleic acid.
ELISA: Enzyme-Linked ImmunoSorbant Assay.
ESIMS: Electrospray Ionization Mass Spectrometry.
Et$_2$O: Diethyl ether.
EtOAc: Ethyl acetate.
F–F$_0$: Fluorescence intensity subtracted from intensity of an equivalent untreated sample.
H3: Histone 3.
H4: Histone 4.

Histone: One of a family of proteins that bind strongly to DNA to make higher order structures known as nucleosomes and/or chromatin, and that are involved in the regulation of the genetic information encoded in DNA.

HPLC: High pressure liquid chromatography.
HR-ESI-MS: High resolution electrospray ionization mass spectrometry.
IR: Infrared spectroscopy.
LCG: Lucigenin.
LSD1: Lysine specific demethylase 1.

Macrocycle: A single cyclic or multi-cyclic compound having one or more rings with the total number of atoms in each ring ranging from about 3 to about 100, more typically from about 3 to about 75, even more typically from about 3 to about 50. A macrocycle comprising multiple rings may further comprise a spacer, such as an aliphatic or heteroaliphatic chain ranging from 1 to about 10 carbon atoms, heteroatoms, or combinations thereof, which separates the multiple rings from one another.

Macrocyclic Sensor: An entity comprising a macrocyclic compound coupled with a detectable moiety that is capable of interacting with an analyte to produce a detectable signal. The macrocyclic compound and detectable moiety may be coupled covalently or non-covalently.

MMA: Monomethyl arginine.
MP: Melting point.

Naming of peptide and protein sites and their modifications: [Protein name][Residue type][Residue number][modification type].

| Protein Names | Residue Types | Modification Types |
|---|---|---|
| H3: Histone 3 | K: Lysine | ac: acetylated |
| H4: Histone 4 | R: Arginine | me: monomethylated |
| p53: tumor protein 53 | S: Serine | me2: dimethylated |
| | T: Threonine | me3: trimethylated |
| | | me2-a: asymmetrically dimethylated (in case of arginine only) |
| | | me2-s: symmetrically dimethylated (in case of arginine only) |
| | | (Cit): citrullinated/deiminated (in case of arginine only) |
| | | ph: phosphorylated |

NMR: Nuclear Magnetic Resonance.
p53: Tumor protein 53.
PCA: Principal component analysis.

Polypeptide: A polymer in which the monomers are amino acid residues which are joined together through amide bonds. When the amino acids are alpha-amino acids, either the L-optical isomer or the D-optical isomer can be used. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced.

The term "residue" or "amino acid residue" includes reference to an amino acid that is incorporated into a protein, polypeptide, or peptide.

Protein: A molecule, particularly a polypeptide, comprised of amino acids.

PTM=Post-translational modification: The enzymatic processing of a polypeptide chain after translation from messenger RNA and after peptide bond formation has occurred. Examples include phosphorylation, acetylation, methylation, citrullination, crotonylation, butyrylation, ubiquitination, and proline cis-trans isomerization.

PSC4: para-sulfonato calix[4]arene.
PSC6: para-sulfonato calix[6]arene.
sDMA: Symmetric dimethylarginine.

II. Introduction

Disclosed embodiments concern a method for identifying or identifying and quantifying analytes that is specific for many different possible post-translational modification states. Also disclosed are embodiments of an array that determines the concentrations and identities of given analytes. A sensor for use in the disclosed method and array is also disclosed.

III. Macrocyclic Sensor

Particular disclosed embodiments concern a macrocyclic sensor capable of providing the ability to identify or identify and quantify post-translationally modified analytes. The disclosed macrocyclic sensor may be used in the disclosed array, method, and enzymatic assay. In particular disclosed embodiments, the macrocyclic sensor comprises a macrocyclic molecule coupled with a detectable moiety.

A. Macrocyclic Compounds

The macrocyclic compound may be any molecule known to those having ordinary skill in the art to be capable of coupling a detectable moiety either through covalent or non-covalent bonds. In particular disclosed embodiments, the macrocyclic compound may be any single cyclic or multi-cyclic compound having one or more rings with the total number of atoms in each ring ranging from about 3 to about 100, more typically from about 3 to about 75, even more typically from about 3 to about 50. In particular disclosed embodiments, a macrocycle comprising multiple rings may further comprise a spacer, such as an aliphatic or heteroaliphatic chain ranging from 1 to about 10 carbon atoms, heteroatoms, or combinations thereof, which separates the multiple rings from one another. In particular disclosed embodiments, the macrocyclic compound may be selected from calixarenes, cyclodextrins, cucurbiturils, crown ethers, and other similar macrocycles. Exemplary macrocyclic compounds are illustrated below in Formulas 1-4.

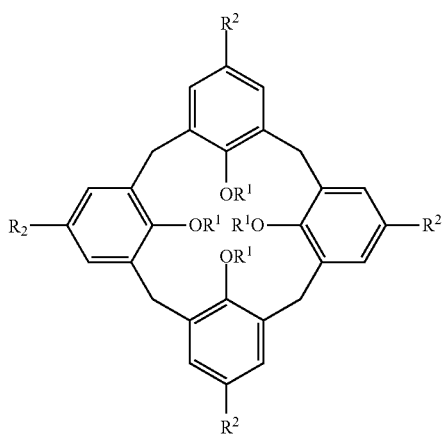

Formula 1

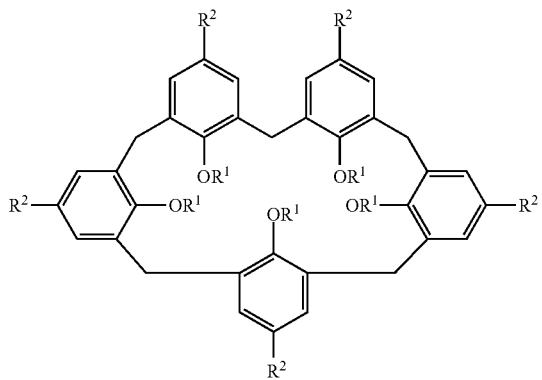

Formula 2

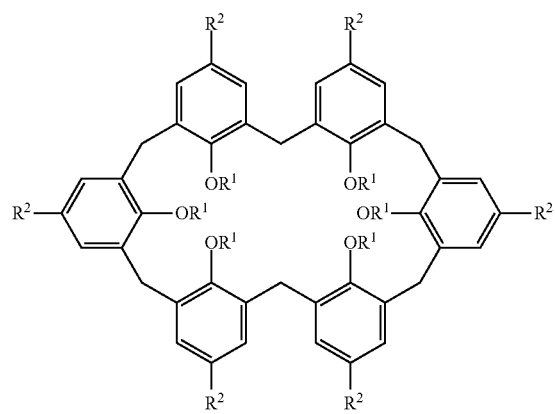

Formula 3

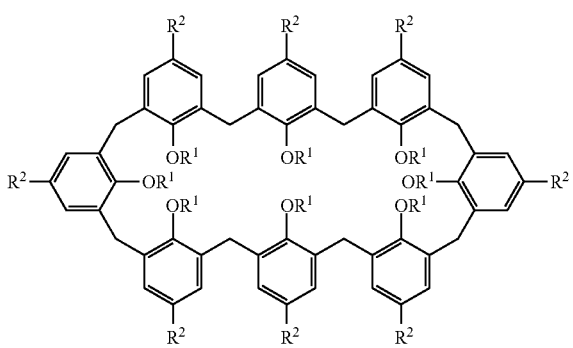

Formula 4

With reference to Formulas 1-4, $R^1$ may be selected from H, aliphatic, such as alkyl, alkenyl, alkynyl; even more typically, $R^1$ may be selected from $(CH_2)_m CH_3$ where m is 0, 1, 2, 3, 4, 5, 6, or 7, or a branched or straight-chain $C_1$-$C_8$-alkyl or $C_1$-$C_8$ alkenyl. $R^2$ may be selected from aliphatic, aromatic, heteroaromatic, and heteroaliphatic. In particular disclosed embodiments, $R^2$ is selected from alkyl, alkenyl, alkynyl, heteroalkyl, heteroalkenyl, and heteroalkynyl. In particular disclosed embodiments, $R^2$ is $(CH_2)_m X$ where m is 0, 1, 2 and X may be selected from F, Cl, Br, I, $SO_3H$, SH, COOH, $NH_2$, $NHR^a$, $NR^a R^b$, $(NR^a R^b R^c)^+$ (in each case where $R^a$, $R^b$ and $R^c$ independently may be selected from aliphatic, particularly alkyl and lower alkyl (e.g., $C_1$-$C_{10}$, such as methyl, ethyl, propyl), or aryl optionally substituted with one or more functional groups selected from cyano, amide, carboxyl, carboxylic acid, amine, alkyl amine, alkyl (e.g., $C_1$-$C_{10}$alkyl, such as methyl, ethyl, propyl, butyl, etc.), alkoxy (e.g., —$OC_1$-$C_{10}$alkyl), halo (such as iodo, fluoro, chloro, or bromo), aldehyde, hydroxyl, alkylhydroxyl (e.g., $C_1$-$C_{10}$hydroxyl), and combinations thereof.

Additional embodiments concern macrocyclic compounds having any one of Formulas 5-7, illustrated below.

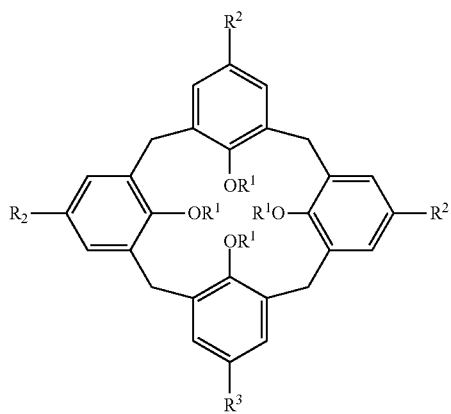

Formula 5

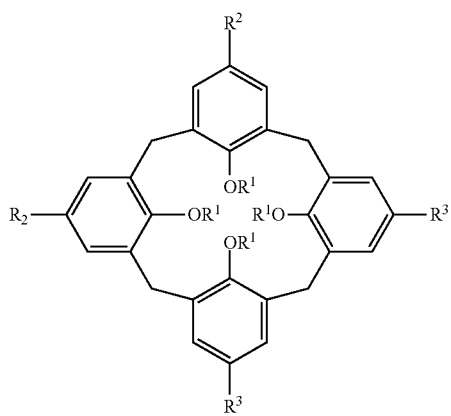

Formula 6

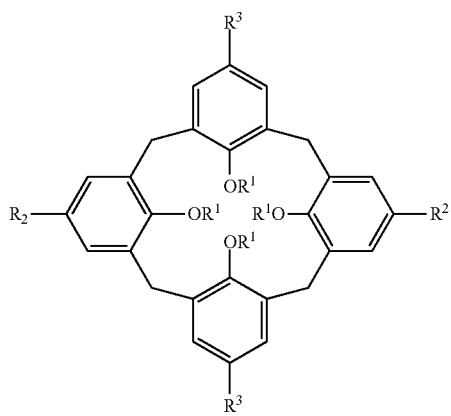

Formula 7

With reference to Formulas 5-7, $R^1$ may be selected from H, aliphatic, such as alkyl, alkenyl, and alkynyl; more typically, $R^1$ is $(CH_2)_m CH_3$ where m is 0, 1, 2, 3, 4, 5, 6, or 7, or a branched or straight-chain $C_1$-$C_8$-alkyl or $C_1$-$C_8$ alkenyl. $R^2$ may be selected from $SO_3H$, $CO_2H$, $PO_3H_2$, and other common functional groups that are anionic in water. $R^3$ may be selected from halogen (such as F, Cl, Br, I), aryl, heteroaryl, and heteroaliphatic. In certain additional embodiments, $R^3$ may be aryl, heteroaryl, and heteroaliphatic optionally substituted with one or more functional groups selected from cyano, amide, carboxyl, carboxylic acid, amine, alkyl amine, alkyl (e.g., $C_1$-$C_{10}$alkyl, such as methyl, ethyl, propyl, butyl, etc.), alkoxy (e.g., —$OC_1$-$C_{10}$alkyl), halo (such as iodo, fluoro, chloro, or bromo), aldehyde, hydroxyl, alkylhydroxyl (e.g., $C_1$-$C_{10}$hydroxyl), and combinations thereof. In particular disclosed embodiments, $R^3$ may be selected from $NH_2$, $NHR^a$, $NR^a R^b$, $(NR^a R^b R^c)^+$ (in each case where $R^a$, $R^b$ and $R^c$ independently may be selected from aliphatic, particularly alkyl (such as methyl, ethyl, propyl), aryl, or $(CH_2)_m$-alkyl where m=0, 1, or 2 and alkyl is branched, straight-chain, or cyclic $C_1$-$C_8$-alkyl or $C_1$-$C_8$ alkenyl). In particular disclosed embodiments, $R^a$, $R^b$, and $R^c$ independently may be heteroaliphatic, such as —$SO_2$aryl wherein the aryl group may be substituted with one or more functional groups selected from cyano, amide, carboxyl, carboxylic acid, amine, alkyl amine, alkyl (e.g., $C_1$-$C_{10}$alkyl, such as methyl, ethyl, propyl, butyl, etc.), alkoxy (e.g., —$OC_1$-$C_{10}$alkyl), halo (such as iodo, fluoro, chloro, or bromo), aldehyde, hydroxyl, alkylhydroxyl (e.g., $C_1$-$C_{10}$hydroxyl), and combinations thereof.

Additional macrocyclic compounds may have any one of Formulas 8-10, illustrated below.

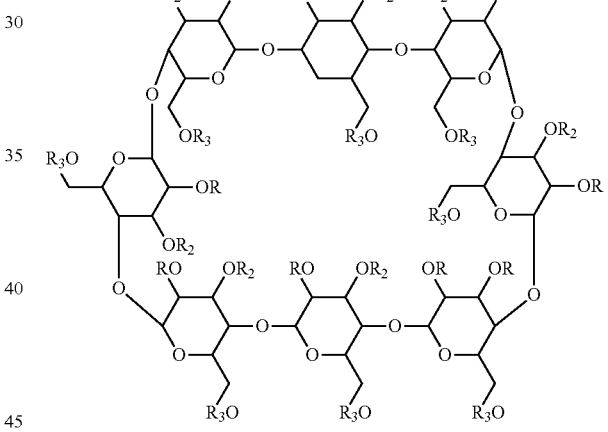

Formula 8

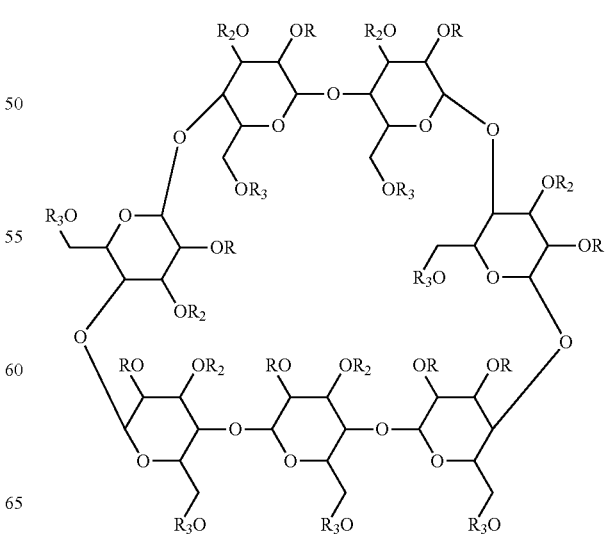

Formula 9

-continued

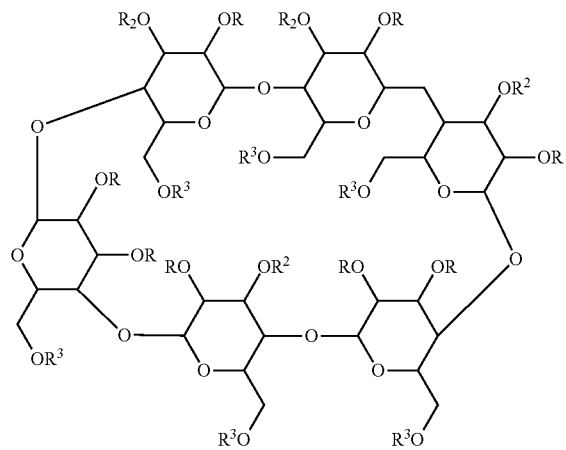

Formula 10

With reference to Formulas 8-10, each R, $R^2$, $R^3$ may be selected from H, aliphatic, such as alkyl, alkenyl, and alkynyl, heteroaliphatic, such as heteroalkyl, heteroalkenyl, and heteroalkynyl, and aryl. In particular disclosed embodiments, $R^3$ may be selected from methyl, ethyl, n-propyl, i-propyl, butyl, octyl, $(CH_2)_{1,2}COOH$, $(CH_2)_{2,3}OH$, acetyl, benzoyl, sulpho, succinyl, and in place of $OR^3$ might be an $NH_2$, $NHR^a$, $NR^aR^b$, $(NR^aR^bR^c)^+$ (in each case where $R^a$, $R^b$ and $R^c$ independently may be selected from aliphatic, aliphatic, such as alkyl, alkenyl, and alkynyl, heteroaliphatic, and aryl; particularly, methyl, ethyl, n-propyl, i-propyl, aryl, $(CH_2)_{1,2}COOH$, $(CH_2)_{2,3}OH$, acetyl, benzoyl, sulpho, succinyl).

Additional embodiments of the disclosed macrocyclic compounds may have any one of the structures illustrated below, wherein the "R" substituent of the general cucurbituril structure may be selected from H, methyl, or hydroxyl.

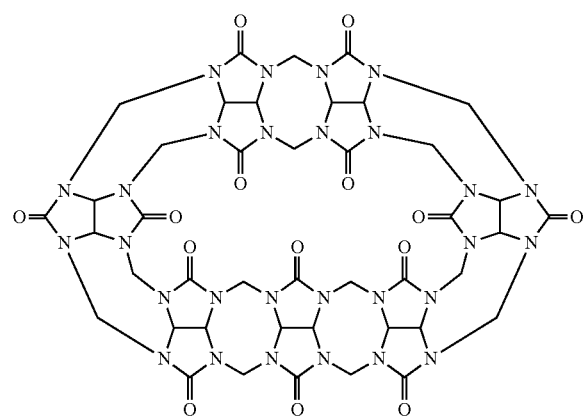

cucurbit[7]uril

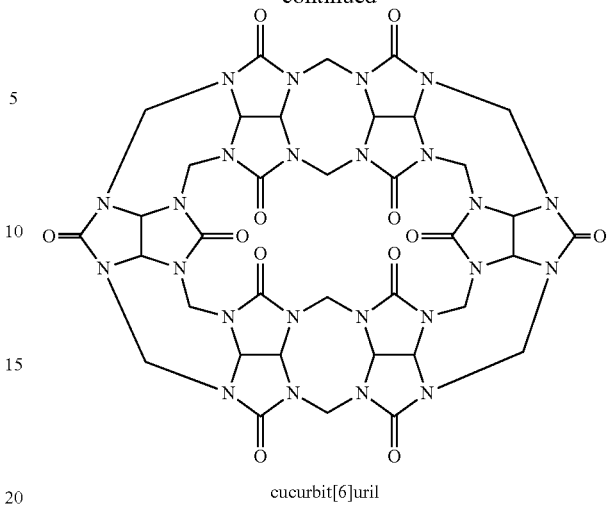

cucurbit[6]uril

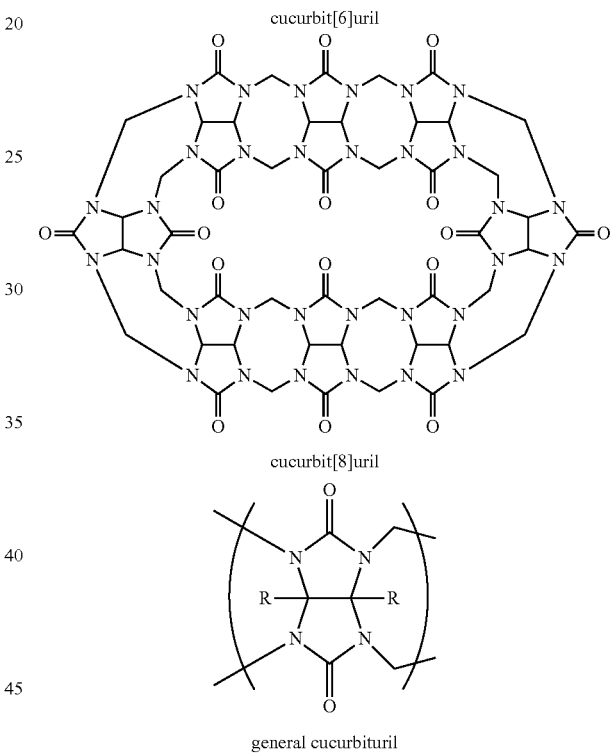

cucurbit[8]uril general cucurbituril

B. Detectable Moieties

The detectable moiety may be selected from compounds capable of producing a signal, such as by fluorescence, absorption, and the like. In particular disclosed embodiments, the detectable moiety may be a dye selected from members of the lucigenin family, members of the fluorescein family, naphthalene-based dyes, pyrene-based dyes, and members of the azole family. In particular disclosed embodiments, the detectable moiety is selected from fluorescein, fluorescein isothiocyanate, rhodamine, tetramethyl rhodamine isothiocyanate (TRITC), naphthalimide, 4-dimethylaminonaphthalimide (4-DMN), coumarin, cyanine, dansyl, PSP, thiazole orange, Oregon green, eosin, Texas red, Cal Fluor, indocarbocyanine, oxacarbocyanine, thiacarbocyanine, merocyanine, Quasar dyes, prodan derivatives, pyridyloxazole, nitrobenzoxadiazole, benzoxadiazole, cascade blue, Nile red, Nile blue, cresyl violet, oxazine 170, proflavin, acridine orange, acridine yellow, auramine, crystal violet, malachite green, porphyrin, phtalocyanine, and bilirubin.

Exemplary dyes used in the disclosed macrocyclic sensor are illustrated below.

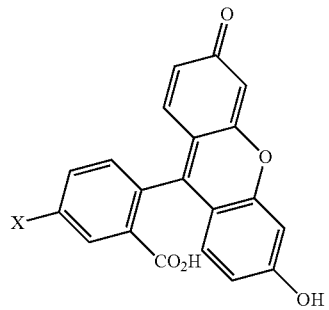
Formula 11

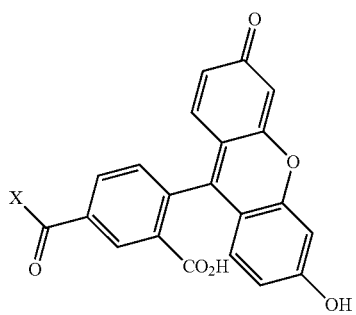
Formula 12

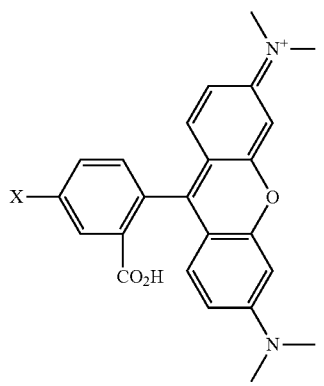
Formula 13

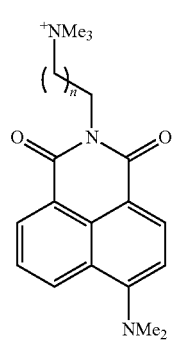
Formula 14

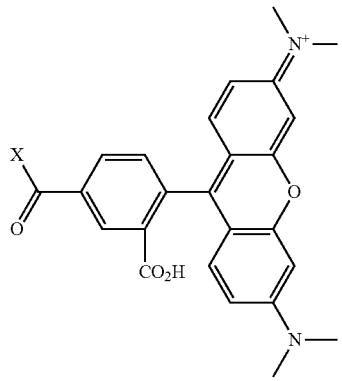
Formula 15

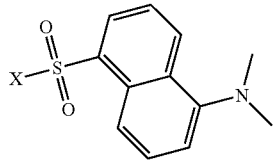
Formula 16

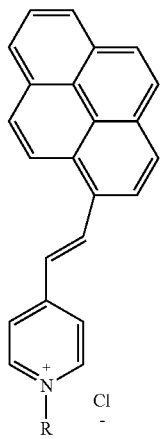
Formula 17

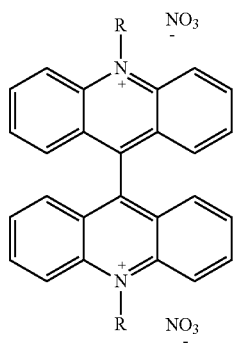
Formula 18

With reference to Formulas 11-18, X may be selected from $NH_2$ or OH. In particular disclosed embodiments, X may indicate N- or O-based covalent linkage to the disclosed macrocyclic compounds. R may be selected from methyl, ethyl, n-propyl, i-propyl, butyl, s-butyl, i-butyl, or t-butyl. With reference to Formula 14, n may be any number from 0-10.

C. Non-Covalently Bound Macrocyclic Sensors

Figure 2:
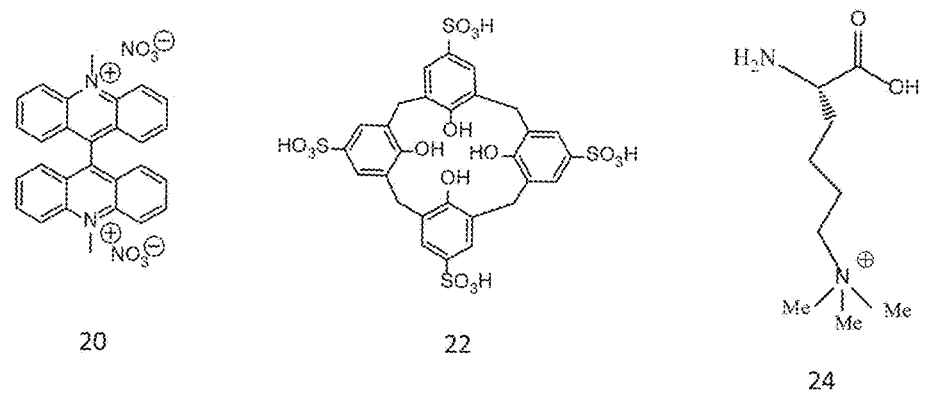
FIG. 2 is an image of a fluorescence emission spectrum illustrating exemplary optical signals that arise using the disclosed method and/or array.
Figure 2:
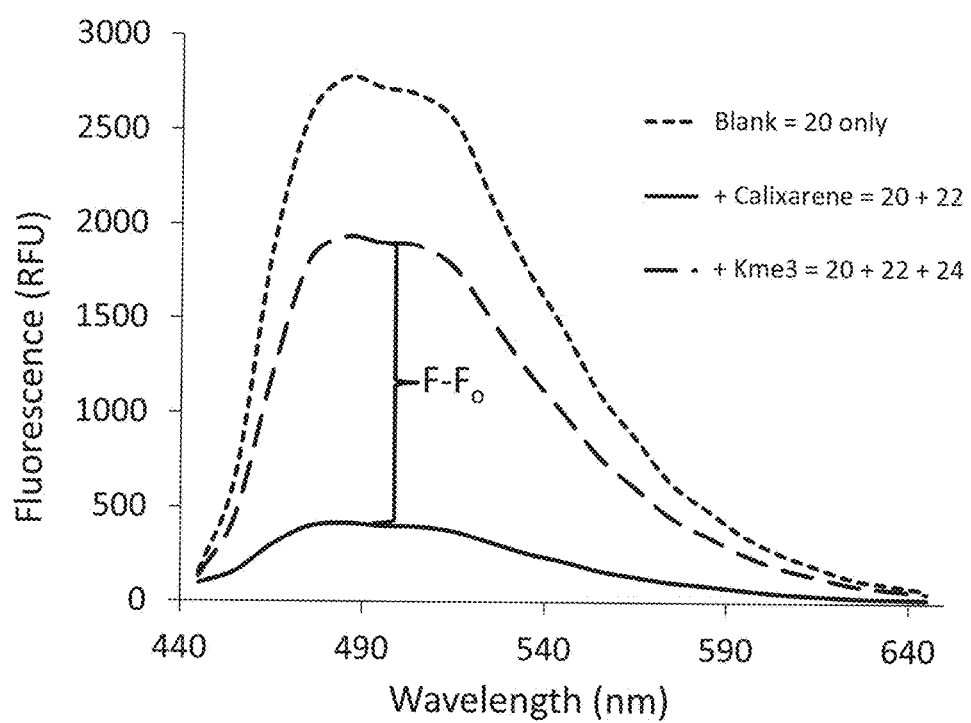
Figure 13A:
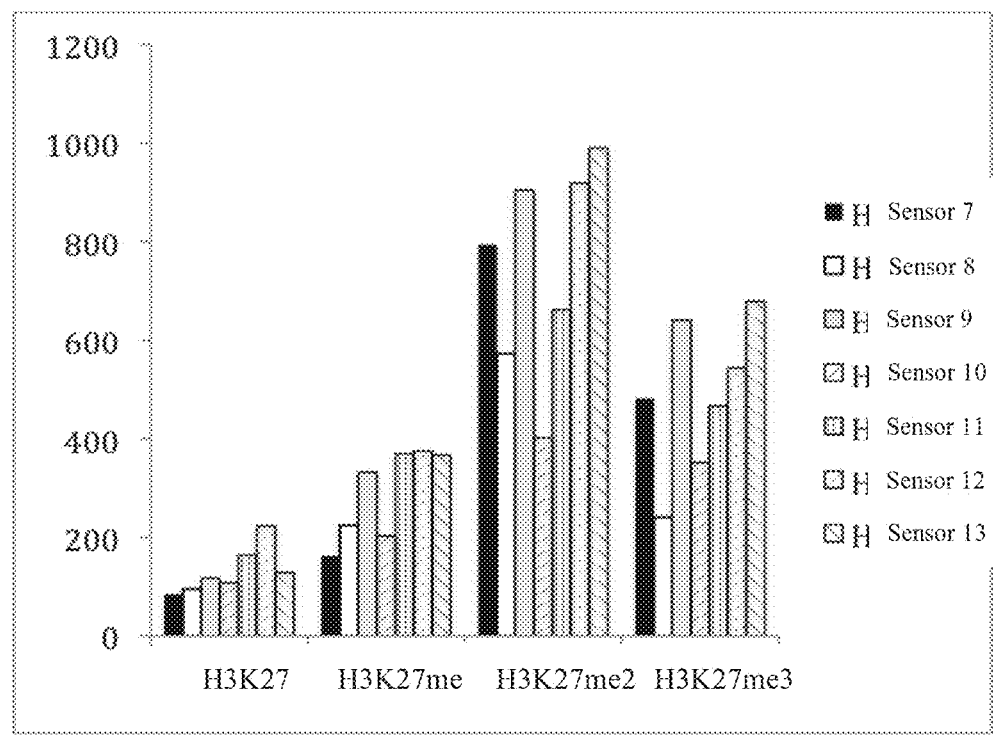
FIGS. 13a and 13b collectively illustrate the ability of the disclosed array and sensors to discriminate closely related analytes on the basis of degree of post-translational methylation, and demonstrate selectivity for lower states of methylation.

In particular disclosed embodiments, the detectable moiety may be coupled either covalently or non-covalently. When the detectable moiety is coupled to the macrocyclic compound non-covalently, a signal may be produced when the detectable moiety is displaced from the macrocycle's binding pocket by an analyte that competes by reversible binding with the macrocyclic compound. FIG. 1a illustrates a particular disclosed embodiment wherein the macrocycle and the detectable moiety are non-covalently bound (2) and the analyte (4) displaces the detectable moiety (8) to give an analyte-macrocyclic compound complex (6). Also, FIG. 2 illustrates a particular embodiment wherein the signals arising from (a) the detectable moiety alone (20), (b) the macrocyclic sensor (22), and (c) a mixture of the detectable moiety (lucigenin), macrocycle(calixarene), and analyte (Kme3,[24]) as illustrated. As FIG. 2 illustrates, a difference in signal is observed when the macrocyclic sensor is exposed to the analyte (note the change between the intensity of the dashed line and the solid line). Selectivity between analytes by any one sensor that is favorable to the discrimination of multiple analytes when that sensor is incorporated in an array is achievable by suitable functionalization of the macrocyclic sensor. FIG. 13a illustrates responses of a set of sensors that are selective for dimethyllysine over trimethyllysine.

D. Covalently Bound Macrocyclic Sensors

Figure 1B:
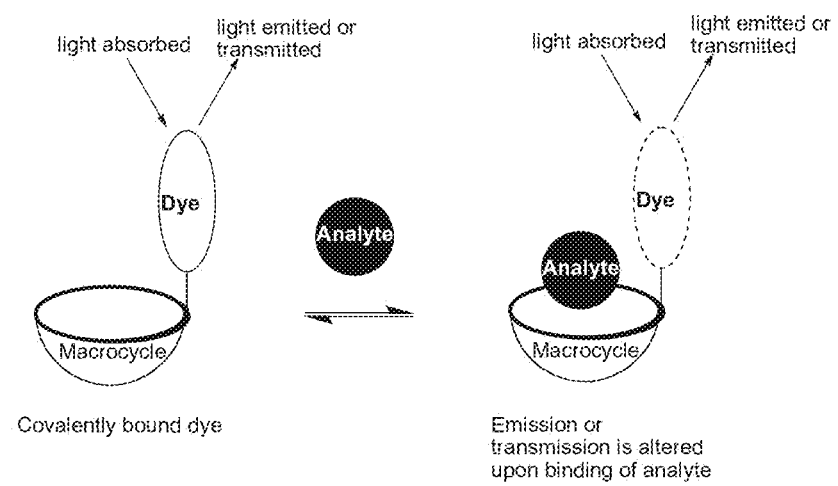
Figure 3A:
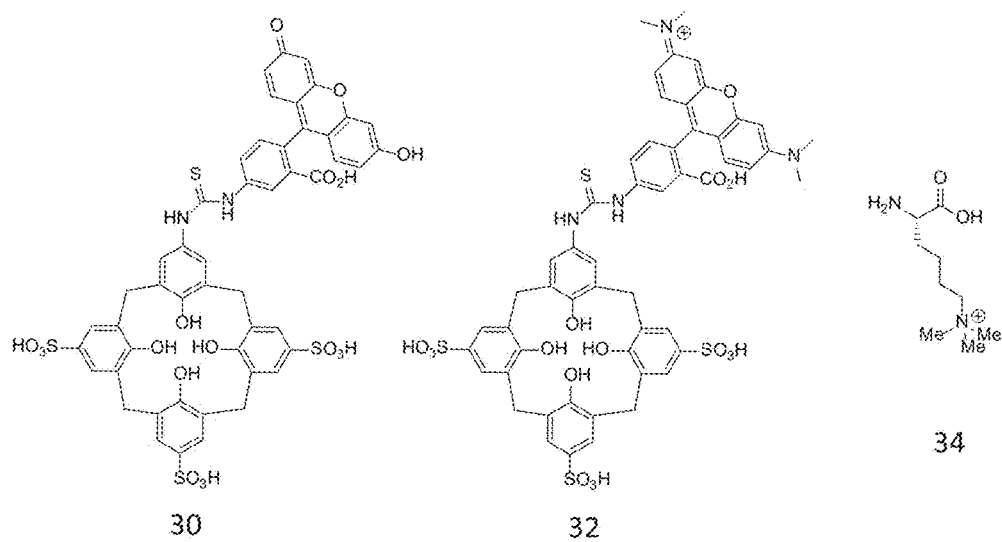
FIGS. 3a and 3b are images of a fluorescence emission spectrum illustrating the effects of an analyte coupling with exemplary embodiments of the disclosed sensor.
Figure 3A:
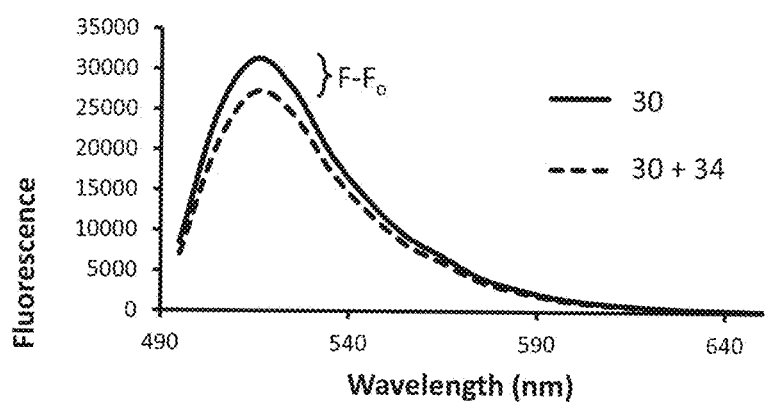
Figure 3B:
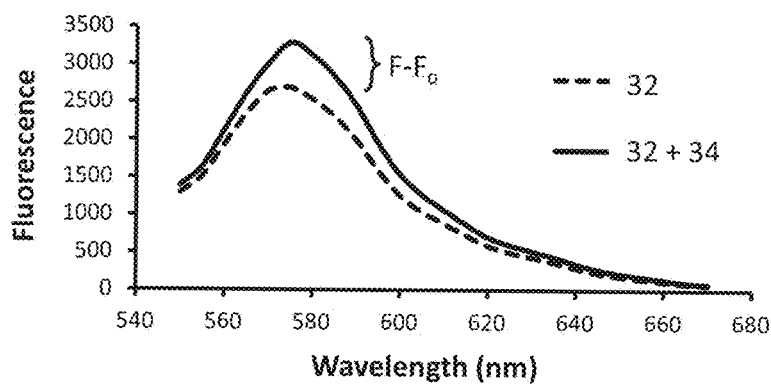

When the detectable moiety is coupled to the macrocyclic compound through a covalent bond a signal may be produced by the detectable moiety when its local environment changes due to proximity effects of the analyte. FIG. 1b illustrates an embodiment wherein the macrocycle and detectable moiety are covalently bound. With reference to FIG. 1b, covalently-coupled sensor 10 reacts with analyte 12 to produce complex 14. Also, FIGS. 3a and 3b illustrate the results obtained from a particular working embodiment. FIG. 3a illustrates the change in fluorescence obtained when a covalently bound macrocyclic probe (30) is exposed to an analyte (34). FIG. 3b illustrates similar results for an additional working embodiment, a TRITC-labeled calixarene sensor (32). Exemplary embodiments of covalently bound macrocyclic sensors are illustrated below.

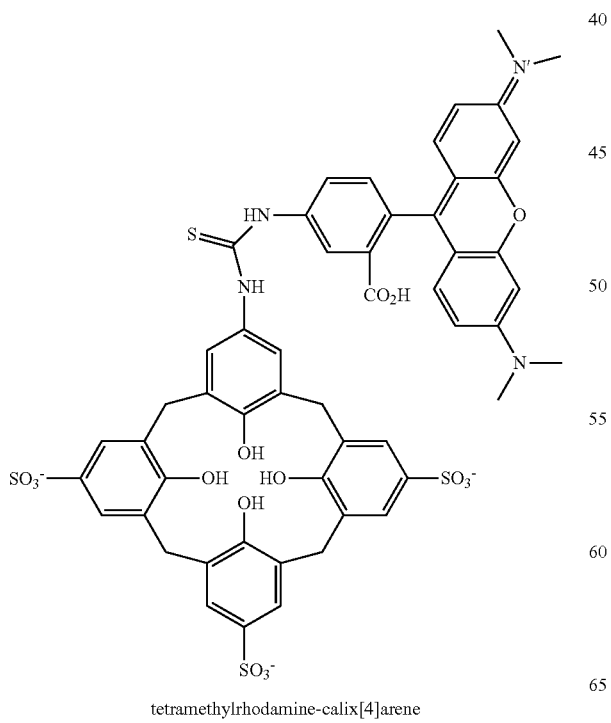

tetramethylrhodamine-calix[4]arene

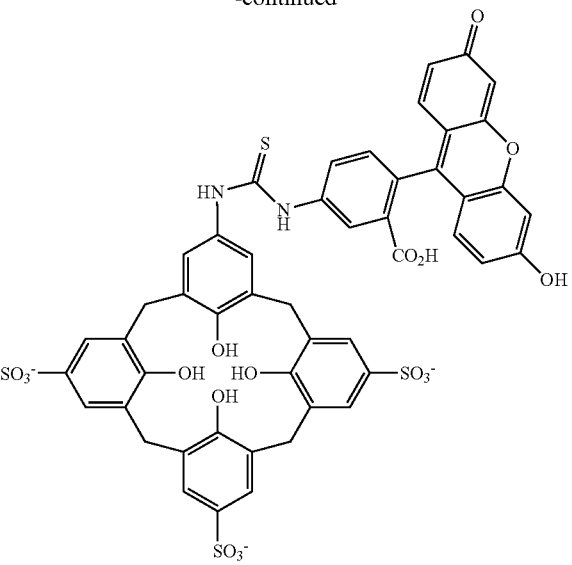

fluorescein-calix[4]arene

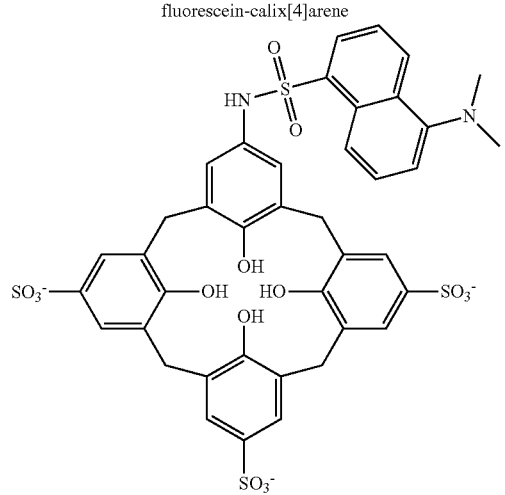

dansyl-calix[4]arene

IV. Analytes

The disclosed method, array, and/or macrocyclic sensor may be used to detect a variety of analytes. In particular disclosed embodiments, the analytes are biological molecules. Of particular interest are analytes that comprise at least one post-translational modification. For example, the analytes may be selected from amino acids, peptides, and proteins that bear at least one post-translational modification. Particular disclosed embodiments concern identifying or identifying and quantifying histones and their post-translational modifications.

Figure 4:
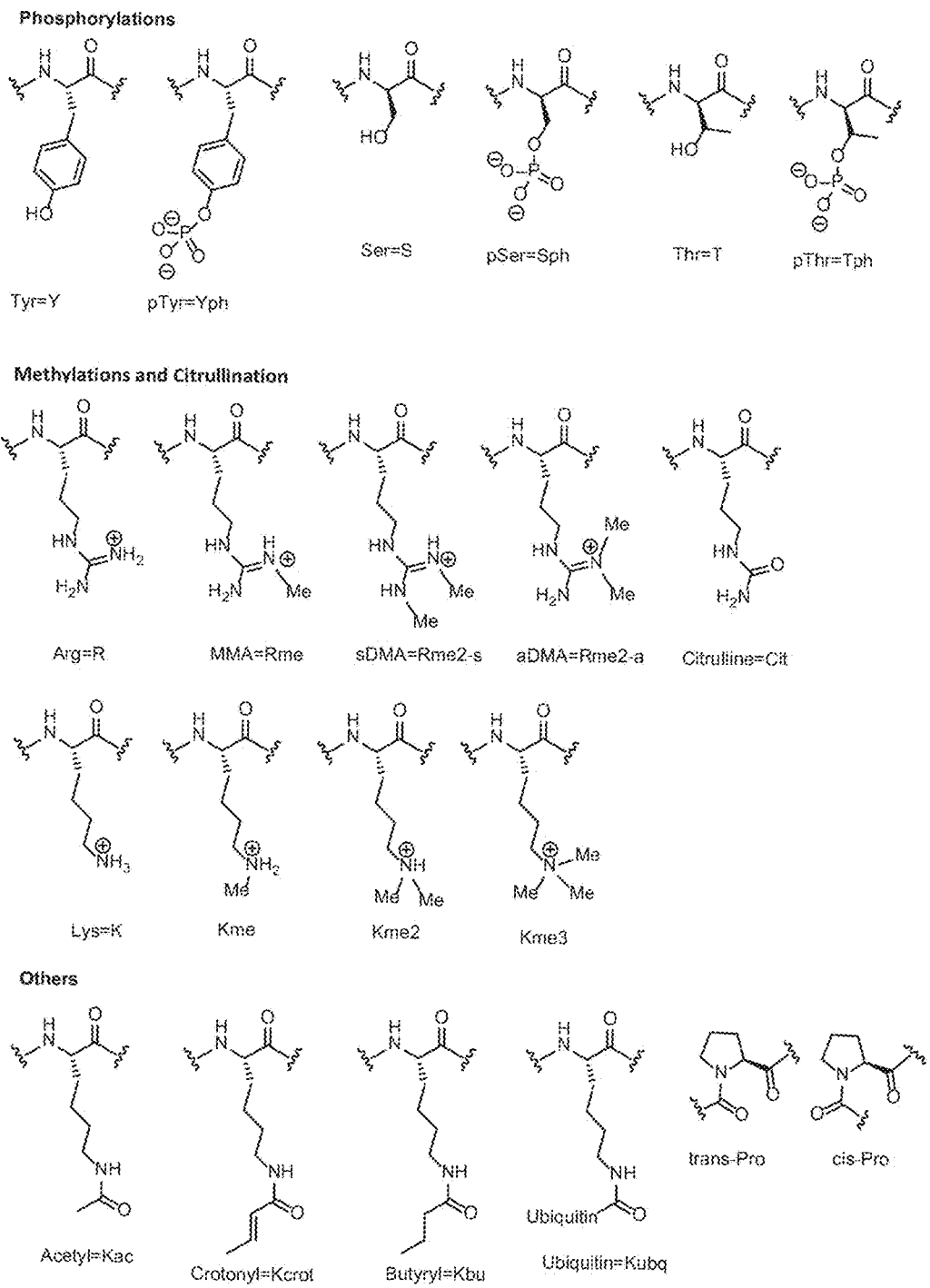
FIG. 4 illustrates various different post-translational modifications.

In particular disclosed embodiments, the analyte comprises at least one post-translationally modified peptide or protein. Several different types of post-translational modifications are contemplated by the present disclosure. In particular, the disclosed macrocyclic sensors may be used to detect one or more of the following: phosphorylations, methylations, acetylations, citrullinations, butyrylations, crotonylations, ubiquitinations, and proline cis-trans isomerizations. This list is merely meant to be exemplary and is not limited to those particular PTMs disclosed therein. FIG. 4 illustrates the products obtained after various different PTMs of particular amino acid side-chains within a peptide and/or protein sequence.

V. Macrocyclic Sensor Array and Method of Use

Figure 7A:
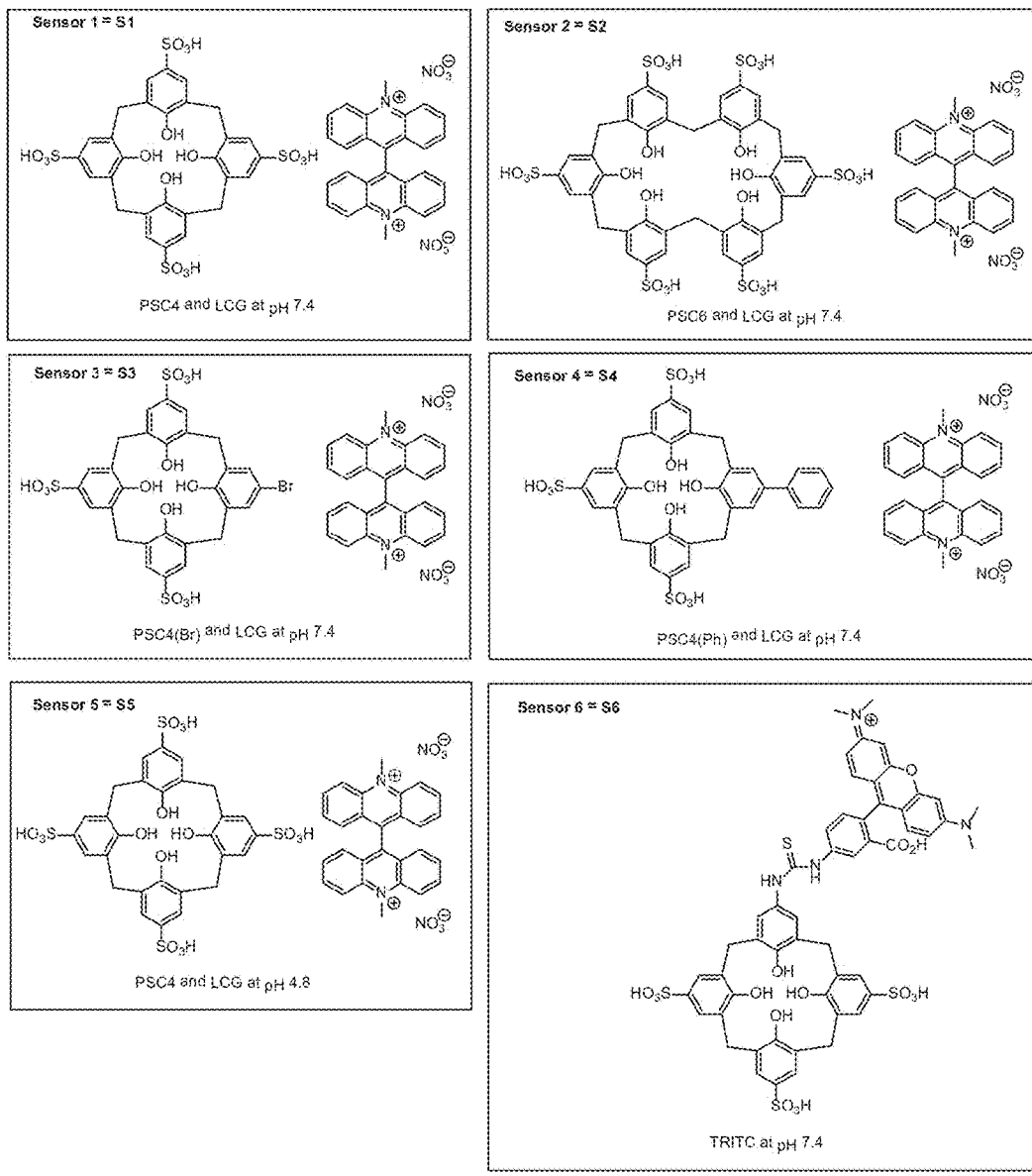
FIGS. 7a and 7b illustrate the structures of various different exemplary sensors used in the disclosed method and array.
Figure 7B:
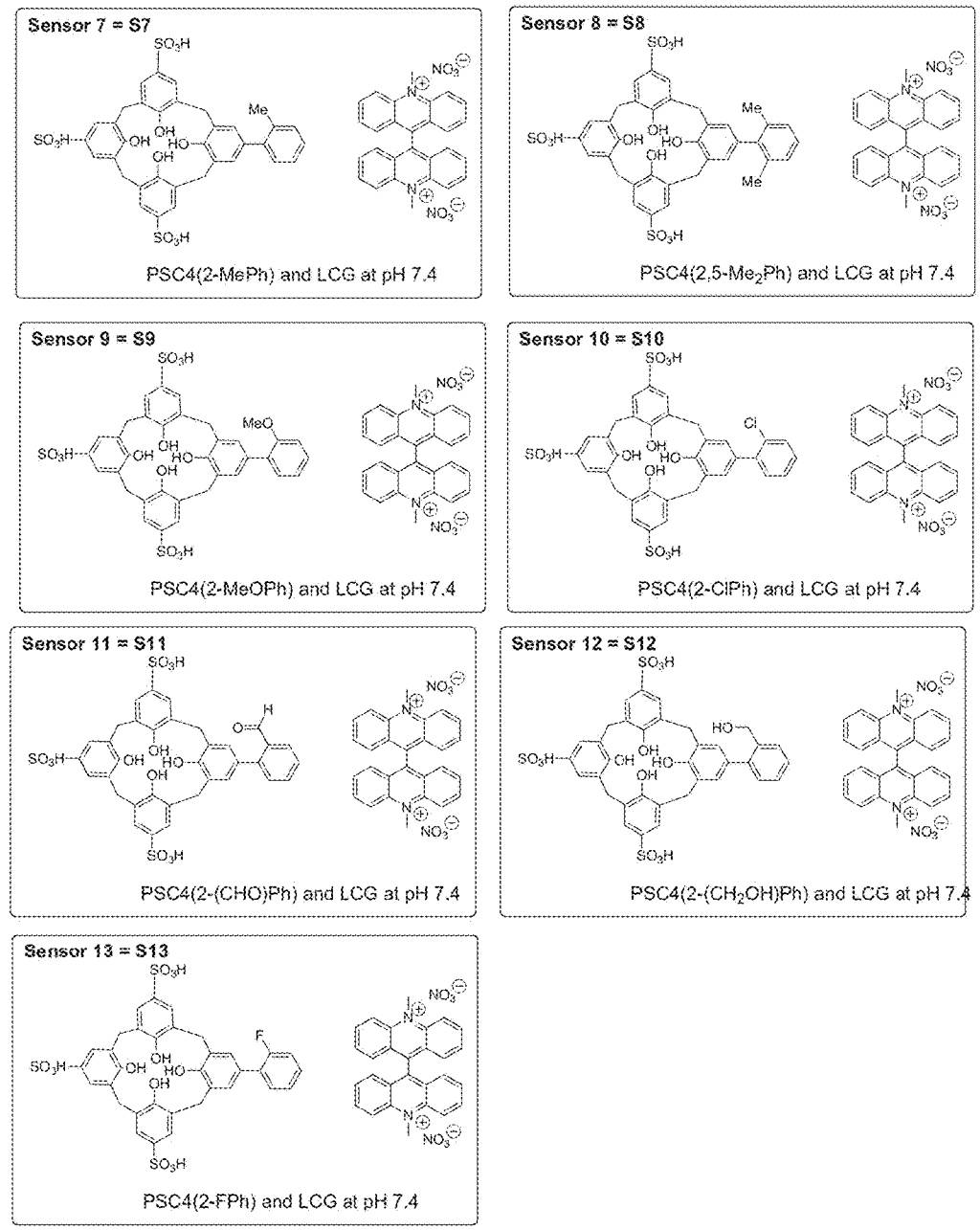

Particular disclosed embodiments concern a macrocyclic sensor array that may be used to identify or identify and quantify one or more post-translationally modified analytes. The disclosed macrocyclic sensor array comprises at least two macrocyclic sensors wherein the at least two different macrocyclic sensors are capable of identifying or identifying and quantifying an analyte having at least one post-translational modification. Examples of exemplary macrocyclic sensors are illustrated in FIGS. 7a and 7b. The combination of data from at least two or more macrocyclic sensors provides information in the form of a signal or a pattern of signals, such as optical signals, that can be correlated to the identity and/or concentration of one or more post-translationally modified analytes. Particular embodiments concern an array comprising two or more different macrocyclic sensors that have differential responses to the targeted analytes. By generating and analyzing a pattern of optical signals from multiple macrocyclic sensors in an array, it is possible to use the disclosed array to determine the identity and/or concentration of the post-translationally modified analyte. Without being limited to a particular theory of operation, it is currently believed that the at least two different macrocyclic sensors respond in different ways to the different post-translationally modified analytes, and that the pattern of responses provides a unique fingerprint that identifies the analyte in question.

In particular disclosed embodiments, the raw data can be manipulated in various ways that facilitate the calibration and visualization of the data for the convenience of end-users. In particular disclosed embodiments, the optical signal obtained from the array may provide patterns that may be used to identify or identify and quantify the analyte. Particular embodiments concern using chemometric methods to manipulate the patterns, such as, but are not limited to, principal component analyses (PCA), linear discriminant analyses (LDA), multilinear regressions, and neural network analyses, the details of which are known to persons having ordinary skill in the art.

Particular disclosed embodiments concern using the macrocyclic sensor array to determine the identity of a post-translational modification present on one analyte, such as a peptide or protein sequence. The macrocyclic sensor array can identify members from a group that are composed of a single sequence bearing different modifications at a single site (e.g. peptides bearing a lysine residue that is unmodified, or modified by acetylation, monomethylation, dimethylation, or trimethylation). The identities of these marks and their relative quantities at a certain modification site may be used as prognostic indicators of numerous human diseases.

Post-translational modifications that are important for biological processes occur at different sites on different peptides and proteins that are defined by having different sequences of amino acids in the local environment of the modification site. Another exemplary use of the macrocyclic sensor array is for determining the identity of the peptide or protein sequence among a set of peptides or proteins that all bear the same post-translational modification within different sequence contexts (e.g. multiple different peptides each bearing a common trimethyllysine mark but having different sequences). The identities of these marks and their relative quantities at different modification sites may be used as prognostic indicators of numerous human diseases.

In particular disclosed embodiments, a method for using the disclosed macrocyclic sensor array is disclosed. According to the disclosed method, a sample comprising at least one analyte having a post-translational modification is provided and then exposed to at least two macrocyclic sensors, and detecting a signal produced by interaction between the at least one analyte and the at least two macrocyclic sensors. In particular disclosed embodiments, exposing the sample to at least two macrocyclic sensors comprises combining the sample with separate solutions wherein each separate solution comprises one of the at least two macrocyclic sensors. Typically, the at least two macrocyclic sensors are not the same. The signal produced by the reaction/interaction between the analyte and the macrocyclic sensor may be an optical signal and such signal may be detected using any method known to those having ordinary skill in the art for measuring fluorescence or absorbance. The disclosed method may further comprise manipulating the data obtained from detecting the signal. Particular disclosed embodiments concern using a chemometric method to manipulate the data, such as (but not limited to) principal component analysis (PCA), linear discriminant analyses, multilinear regressions, and neural network analyses. This type of analysis may be done with commercially available software using a computer.

Representative results obtained using embodiments of the disclosed array are illustrated in FIGS. 8-16. FIGS. 8-11 collectively illustrate the ability of the disclosed sensors to discriminate between different analytes on the basis of PTM identity.

Figure 8A:
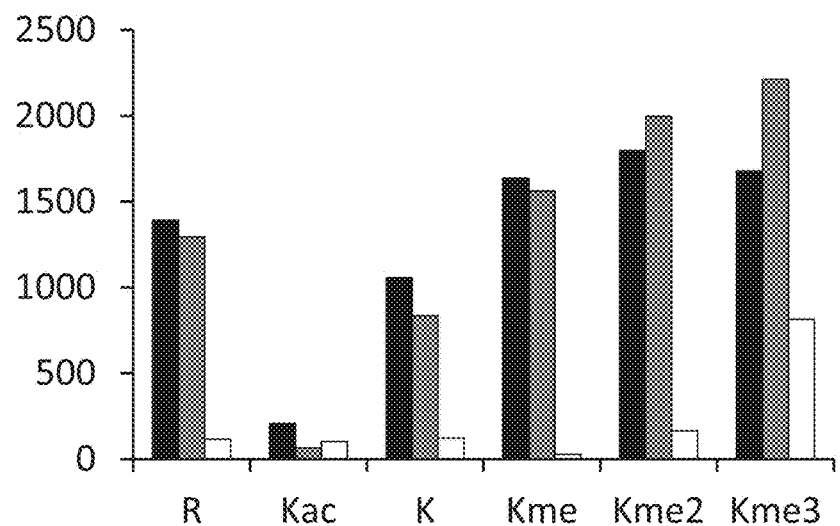
FIGS. 8a and 8b collectively illustrate exemplary results obtained using the disclosed array.
Figure 8B:
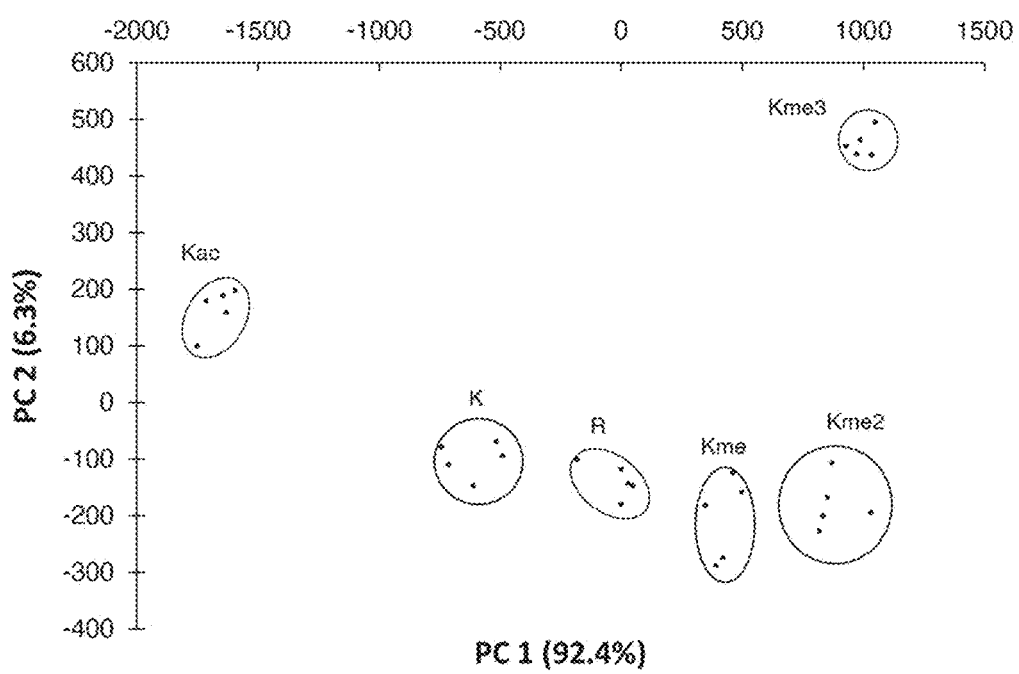

FIGS. 8a and 8b illustrate results obtained from an embodiment of the disclosed macrocyclic sensor array wherein analytes are successfully identified. FIG. 8a illustrates patterns of fluorescence data obtained from analysis of each sensor/analyte combination and FIG. 8b is the plot obtained from principal component analysis of the fluorescence data, which illustrates that the analytes can be differentiated using pattern recognition. With reference to FIGS. 8a and 8b, the analytes examined include Kac, K, Kme, Kme2, Kme3, and R (depicted in FIG. 4) and the macrocyclic sensor array components include Sensors 51 (black)=1.5 uM PSC4, 500 nm LCG in 10 mM phosphate buffer (pH=7.4), S2 (stripe)=1.5 uM PSC6, 500 nm LCG in 10 mM phosphate buffer (pH=7.4), and S5 (white)=1.5 uM PSC4, 500 nm LCG in 10 mM NH4OAc (pH=4.8).

Figure 9A:
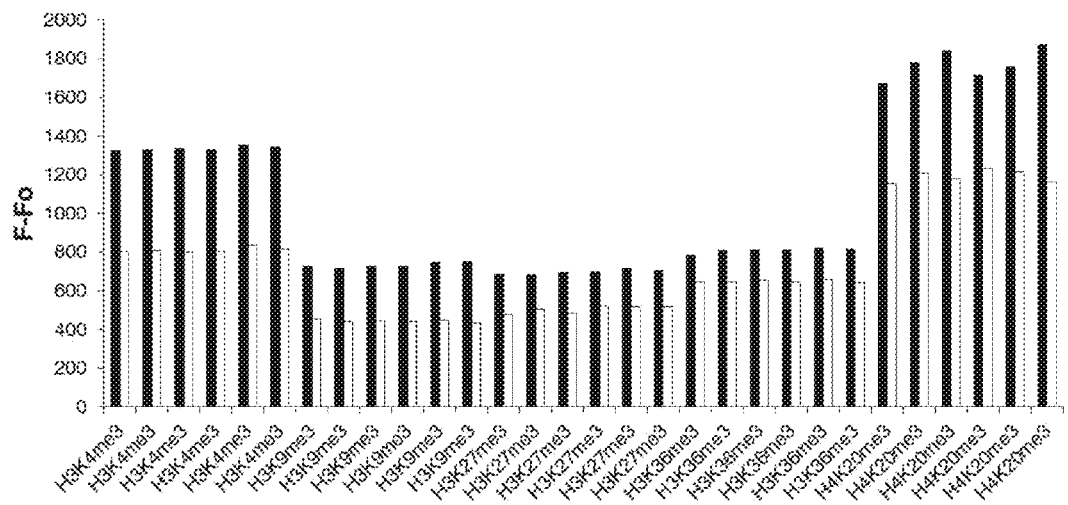
FIGS. 9a and 9b collectively illustrate the ability of the disclosed array and sensors to discriminate closely related analytes on the basis of peptide sequence around post-translational modifications (PTMs).
Figure 9B:
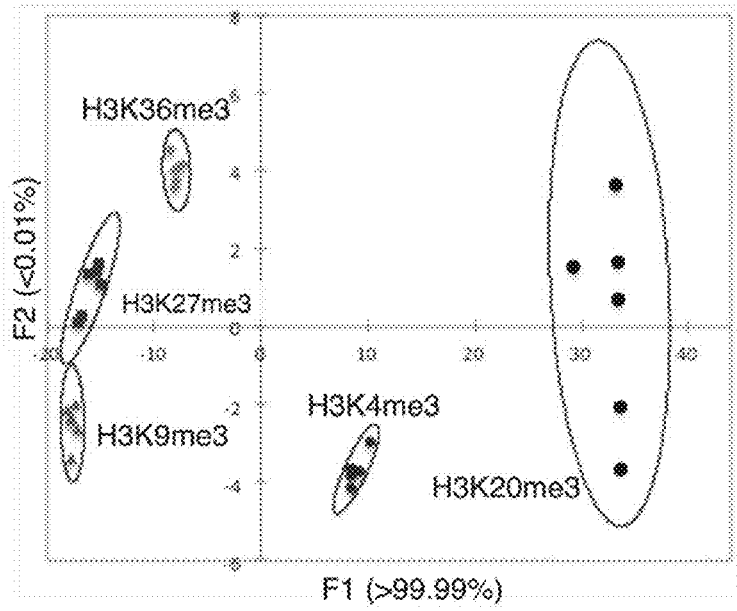

FIGS. 9a and 9b collectively illustrate the ability of the disclosed method and sensors to discriminate closely related analytes on the basis of peptide sequence around PTMs. FIG. 9a illustrates the results obtained from fluorescence analysis of each sensor/analyte combination contained in the array. FIG. 9b is a plot arising from linear discriminant analysis illustrating differentiation of the analytes based on pattern recognition. With reference to FIGS. 9a and 9b, the analytes examined include H3K4me3=peptide H$_2$N-ART(Kme3)QTAY-NH$_2$, H3K9me3=peptide Ac-TAR(Kme3)KSTGY-NH$_2$, H3K27me3=peptide Ac-AAR(Kme3)SAPY-NH$_2$, H3K36me3=peptide Ac-GGV(Kme3)KPHY-NH$_2$, and H4K20me3=peptide Ac-RHR(Kme3)VLRY-NH$_2$ and the macrocyclic sensor array components include Sensors S1 (black)=1.5 uM PSC4, 500 nm LCG in 10 mM phosphate buffer (pH=7.4) and S3 (white)=1.5 uM PSC(Br), 500 nm LCG in 10 mM phosphate buffer (pH=7.4).

Figure 10A:
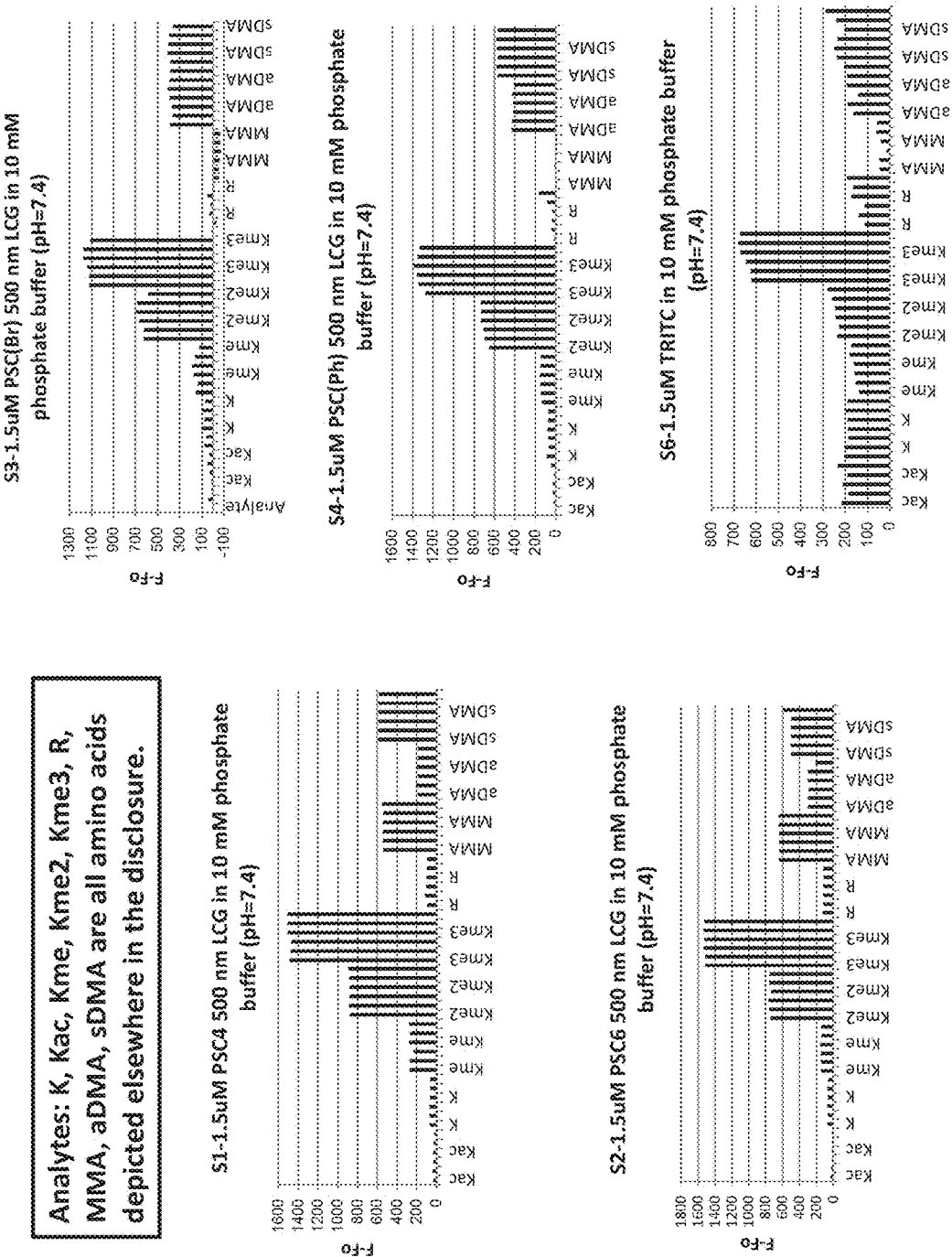
FIGS. 10a and 10b concerns an exemplary embodiment wherein sensor array data discriminates between a large set of closely related amino acid analytes on the basis of PTMs. Raw data is presented for all analytes with each sensor.
Figure 10B:
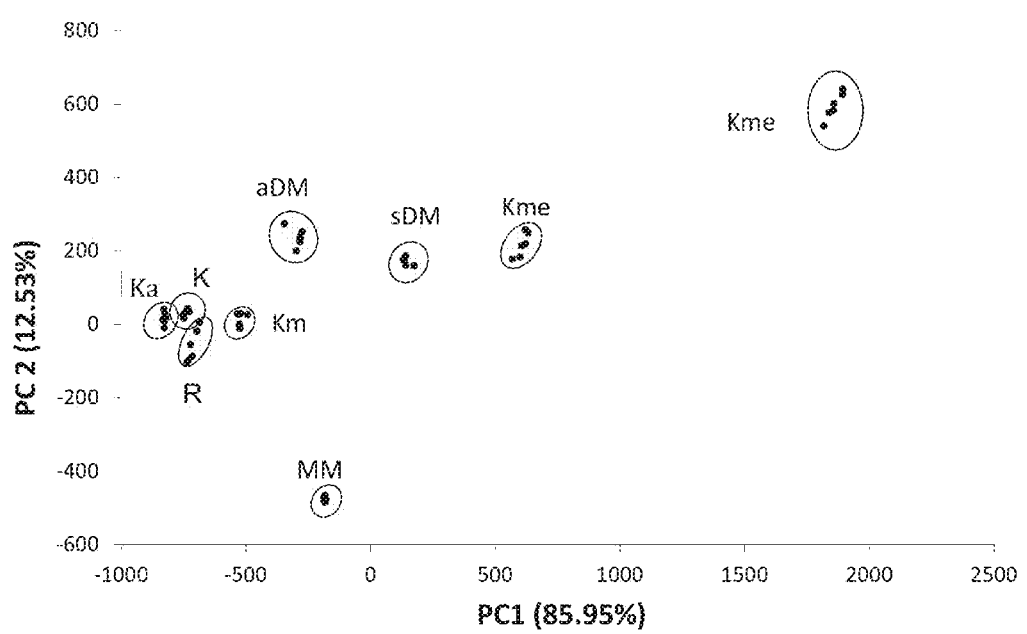
Figure 11:
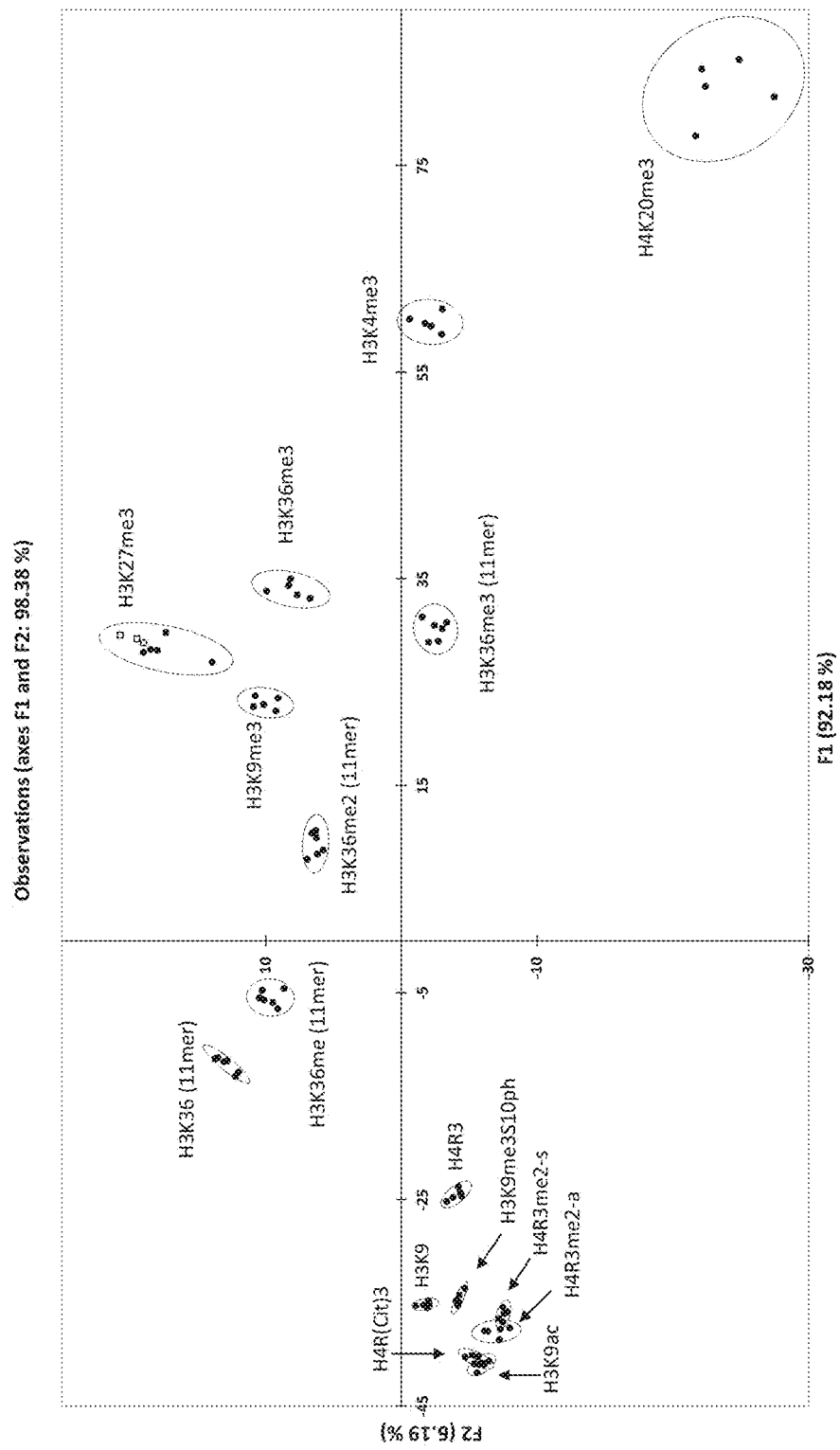
FIG. 11 concerns an exemplary embodiment wherein sensor array data discriminates between a large set of closely related peptide analytes on the basis of PTMs.

FIGS. 10a, 10b and 11 illustrate results obtained from using the macrocyclic sensor array to discriminate amongst a large set (e.g., 9 or more) of closely related analytes on the basis of post-translational modification.

VI. Enzymatic Assay

Particular disclosed embodiments concern using the macrocyclic sensor array for tracking the changes that occur during a biochemical reaction whereby one analyte, such as a peptide or protein, is converted to a product that differs in post-translational modification state. Examples of biochemical reactions of this sort are well known to those having ordinary skill in the art. An exemplary embodiment is an enzyme assay for a methyltransferase enzyme that adds methyl groups to a peptide sequence at a certain lysine site (the substrate). In particular disclosed embodiments, the macrocyclic sensor array can be used to report changes in concentration that arise from activity of the enzyme on the substrate. The outputs produced from using the macrocyclic sensor array can be used to provide information on both the progress of the reaction and the identity of the product of the enzymatic reaction. The macrocyclic sensor array can therefore be used in an enzymatic assay in order to identify or identify and characterize compounds that alter the course of the enzymatic reaction. Examples of typical alterations include, but are not limited to, inhibiting the enzyme resulting in a slower rate of reaction, activating the enzyme resulting in a faster rate of reaction, and modulating the enzyme resulting in a change in the substrate and/or product of the enzymatic reaction. All such alterations are contemplated in the disclosed assay using the disclosed array.

Figure 16A:
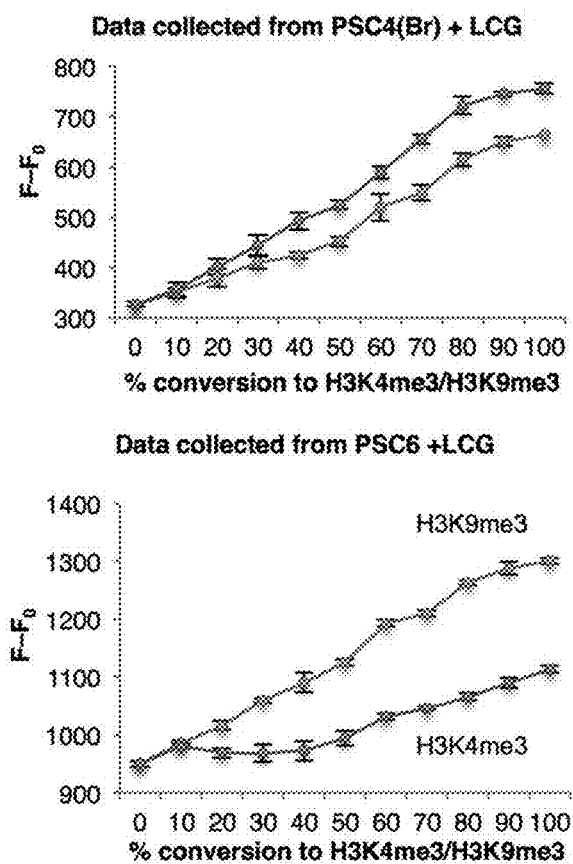
FIGS. 16a and 16b collectively illustrate that sensor array data may be used to track conversions of one analyte to another and provide information on the extent of reaction and identity of each product.
Figure 16B:
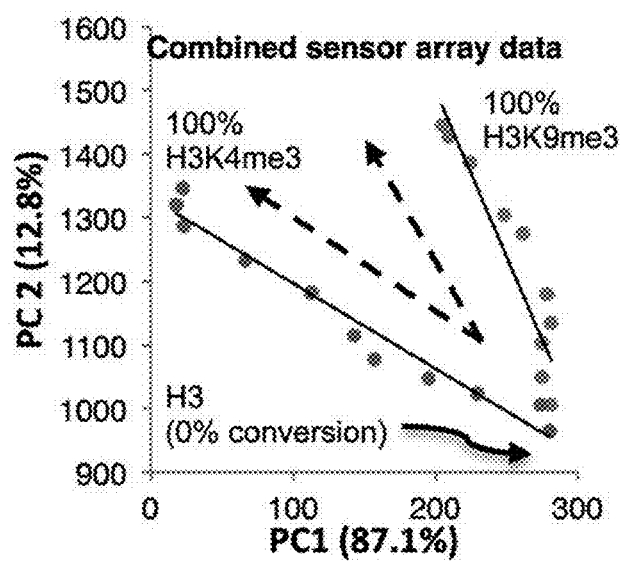

Results from a particular working embodiment using the disclosed enzymatic assay are illustrated in FIGS. 16a and 16b. According to FIGS. 16a and 16b, the disclosed macrocyclic array was used to identify the product of the enzyme-catalyzed conversion of H3 to H3K4me3 and H3K9me3. Scheme 1 illustrates sample reactions of H3 by two different methyltransferases or one methyltransferase under the influence of a modulator that changes the product's identity. Also, Table 1 illustrates the preparation of samples reflecting the extent of reaction. FIG. 16a illustrates the raw data obtained during analysis of the reaction using two different macrocyclic sensors. FIG. 16b provides results from principal component analysis of this particular embodiment and illustrates the ability to track the reaction and provide the identity of each product. With reference to FIG. 16b, the dashed arrows indicate the direction of the data movement upon reaction of the starting material and its conversion to each distinct product.

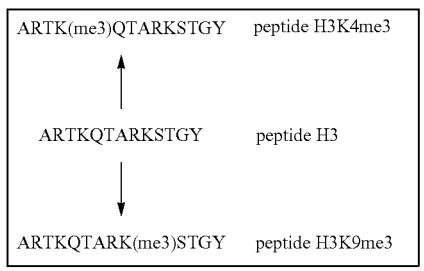

TABLE 1

Sample made up to represent increasing conversion from peptide H3 to H3K4me3 and H3K9me3

| Sample # | % H3 | % H3K4me3 or H3K9me3 |
|---|---|---|
| 1 | 100 | 0 |
| 2 | 90 | 10 |
| 3 | 80 | 20 |
| 4 | 70 | 30 |
| 5 | 60 | 40 |
| 6 | 50 | 50 |
| 7 | 40 | 60 |
| 8 | 30 | 70 |
| 9 | 20 | 80 |
| 10 | 10 | 90 |
|  | 0 | 100 |

VII. Working Embodiments

The following examples are provided to illustrate certain features of working embodiments of the present invention. A person of ordinary skill in the art will appreciate that the invention is not limited to such features. The specific macrocyclic sensors that are used in these one or more of these examples are shown in FIGS. 7a and 7b.

Synthesis and Characterization of Macrocyclic Sensors

Figure 5:
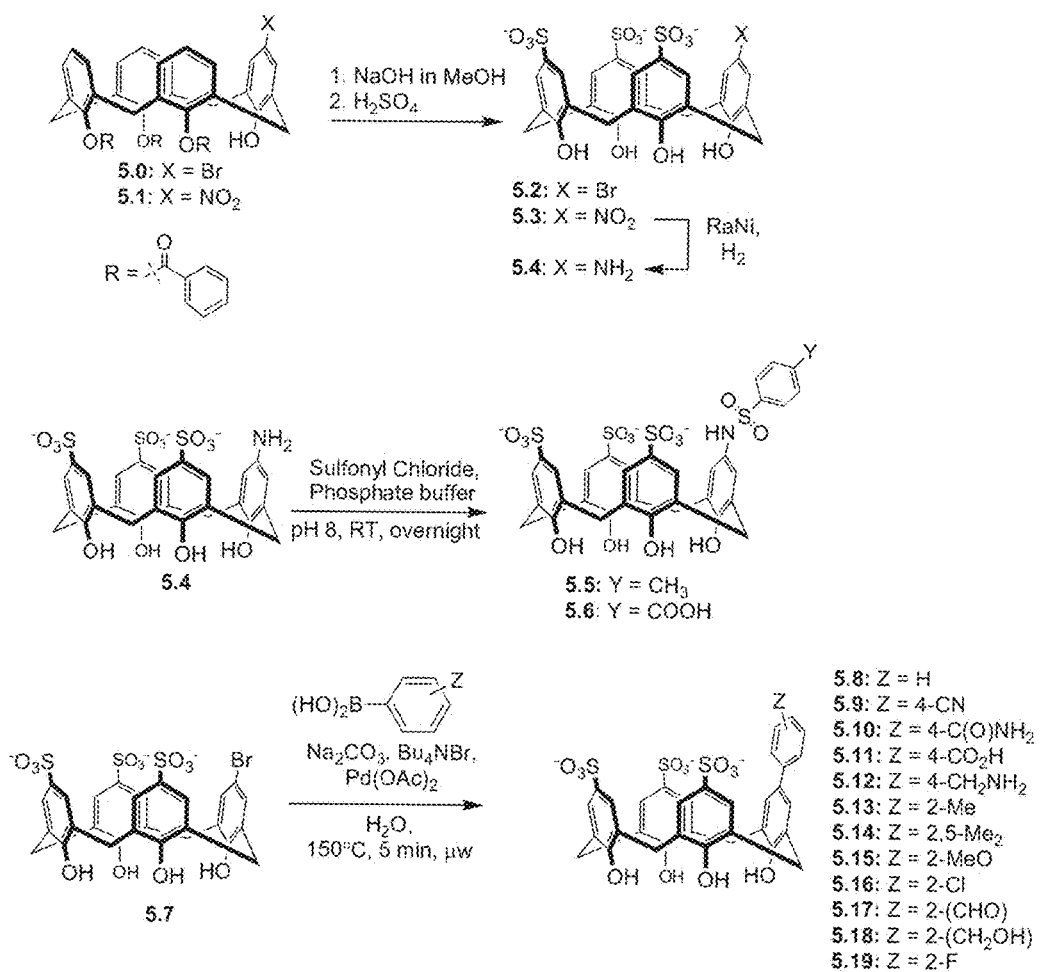
FIG. 5 illustrates the synthesis of various different exemplary macrocycles used to make various embodiments of the disclosed sensor.
Figure 6:
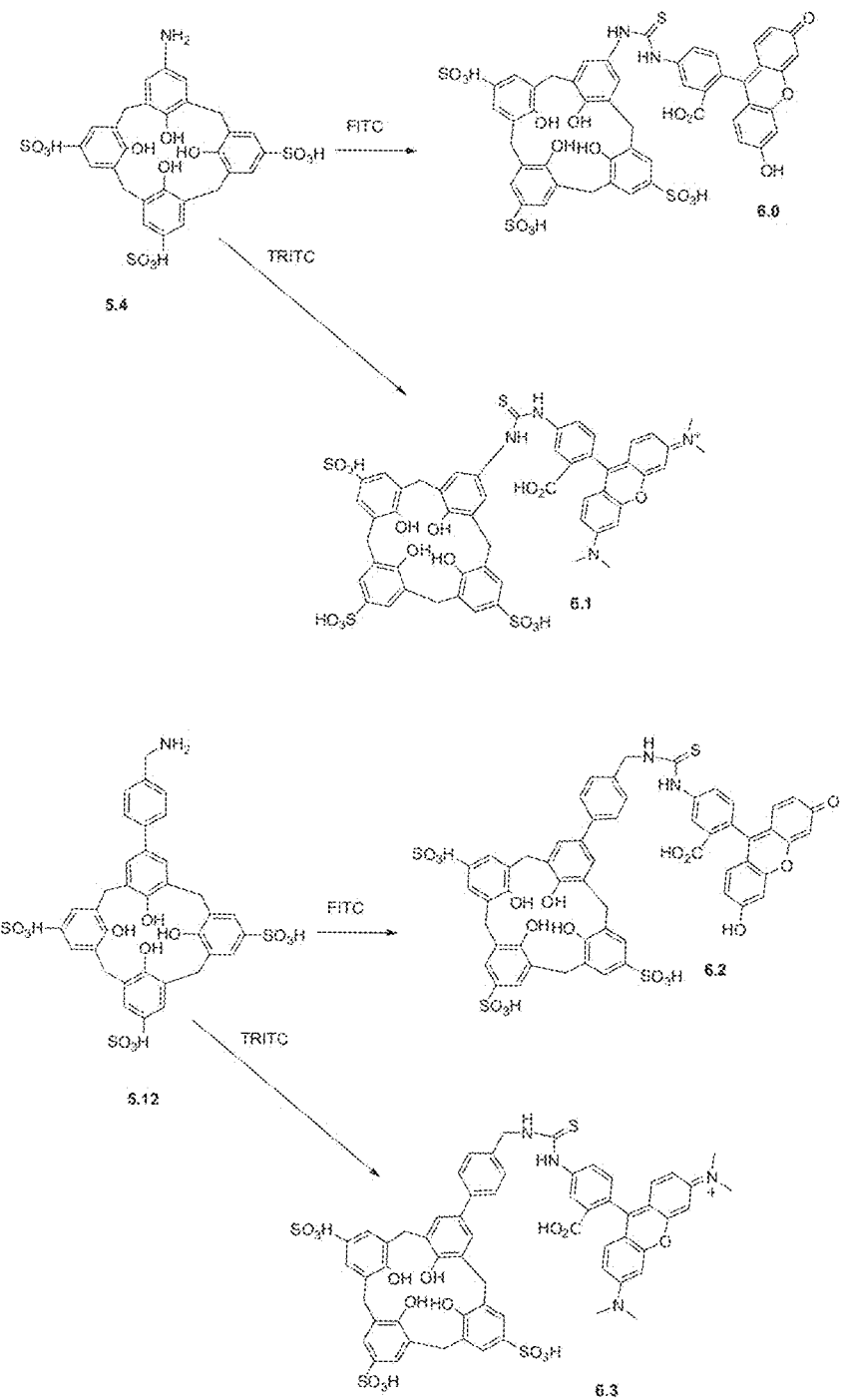
FIG. 6 shows the synthesis of various different exemplary sensors comprising macrocycles covalently attached to dyes.

The following examples are provided to illustrate certain macrocycles that are used as sensing elements in working embodiments of the present invention. A person of ordinary skill in the art will appreciate that the invention is not limited to only these macrocyclic sensors. The schemes used to prepare the exemplary macrocycles are shown in FIGS. 5 and 6.

General Synthetic Information:

Proton nuclear magnetic resonance spectra ($^1$H NMR) were recorded at 500 MHz or 300 MHz at 23° C. unless otherwise stated. Proton chemical shifts are expressed in parts per million (ppm, δ scale) downfield from tetramethylsilane, and are referenced to residual proton in the NMR solvent (CHCl$_3$, δ 7.26; DOH δ 4.79). Data are represented as follows: chemical shift, multiplicity (s=singlet, d=doublet, t=triplet, q=quartet, sext=sextet, m=multiplet and/or multiple resonances, br=broad), coupling constant in Hertz, and integration. Carbon nuclear magnetic resonance spectra ($^{13}$C NMR) were recorded at 125 MHz or 75 MHz at 23° C., unless otherwise stated. Carbon chemical shifts are reported in parts per million downfield from tetramethylsilane and are referenced to residual carbon resonances of the solvent or to the deuterium lock reference in the case of D$_2$O. Infrared (IR) spectra were obtained using a Perkin Elmer 1000 FT-IR spectrometer. Data are represented as follows: frequency of absorption (cm$^{-1}$), intensity of absorption (s=strong, m=medium, w=weak, br=broad). HR-ESI-MS data was obtained on an LTQ Velos Orbitrap or Micromass Q-TOF II. Melting points are uncorrected. Starting compounds 5.0 and 5.1 were made according to Kye Chun Nma, D. S. K. *Bull. Korean Chem. Soc.* 1994, 15, 284-286, and Vezina, M.; Gagnon, J. *Organometallics* 2000, 20, 273-281.

Synthesis of Macrocyclic Sensors that Operate by Reversible Binding of Dyes 5-nitro-25,26,27,28-tetrahydroxy-11-17-23-trisulfonatocalix[4]arene (5.3)

Compound 5.1 (0.78 g, 1.66 mmol) was dissolved in a minimal amount of DCM with an attached reflux condenser and heated to 60° C. Concentrated H$_2$SO$_4$ (1.2 mL, 14 equiv.) was added and stirring was continued for 1 hour. The product is observed to be precipitating out of the reaction mixture during this time. After 1 h, the liquid can be decanted off and the residue washed with numerous amounts of DCM. The product is then suspended in a minimal amount of EtOAc and poured into centrifuge tubes (50 mL) and topped off with Et$_2$O. After two rounds of decanting, re-suspending in Et$_2$O and centrifugation, the off-white powder was dried under vacuum to yield 1.06 g of clean product in 90% yield. Mp: >250° C. (dec). IR (KBr pellet): 3316s br, 1594w, 1521w, 1454w, 1342m, 1211s, 1155s, 1116s, 1040s, 895w, 808w, 786w, 746w, 665w, 651w, 626m, 559m. $^1$H NMR (300 MHz, D$_2$O): δ 7.97 (s, 2H), 7.57 (s, 4H), 7.50 (s, 2H), 3.98 (d, J=3.8 Hz, 8H). $^{13}$C NMR (75 MHz, D$_2$O): δ 155.7, 152.0, 151.5, 141.2, 136.0, 135.8, 128.5, 128.2, 127.7, 126.7, 126.64 (×2), 126.58, 125.16, 30.6, 30.5. HR-ESI-MS: 732.0126 (MNa$^+$, C$_{28}$H$_{23}$NO$_{15}$S$_3$Na$^+$; calcd 732.0128)

5-amino-25,26,27,28-tetrahydroxy-11-17-23-trisulfonatocalix[4]arene (5.4)

5.3 (0.113 g, 0.16 mmol) is dissolved in 10 mL of deionized H$_2$O. Approximately 10 drops of Raney Nickel (2800, slurry in water) is added and the solution is adjusted to pH 8-9 using 2 M NaOH. The solution is stirred at room temperature for 1 hour while H$_2$ gas is bubbled through the solution. After filtration through celite the solution is lyophilized overnight to afford 5.4 as a grey powder in quantitative yield. Mp: 180° C. (dec). IR (KBr pellet): 3445s br, 1471m, 1434m, 1183s, 1113s, 1046s, 892w, 794w, 741w, 671w, 654w, 629m, 548w. $^1$H NMR (300 MHz, D$_2$O): δ 7.69 (d, J=2.4 Hz, 2H), 7.65 (d, J=2.4 Hz, 2H), 7.52 (s, 2H), 7.09 (s, 2H), 4.05 (d, J=3.8 Hz, 8H). $^{13}$C NMR (75 MHz, CD$_3$OD): δ 160.2, 157.7, 145.4, 141.0, 135.9, 134.3, 132.8, 132.1, 131.2, 130.9, 127.3, 127.2, 127.1, 117.6, 34.4, 33.22. HR-ESI-MS: 337.5086 (M−2H$^{2-}$, C$_{28}$H$_{23}$NO$_{13}$S$_3^{2-}$; calcd 337.5088).

5-bromo-25,26,27,28-tetrahydroxy-11-17-23-trisulfonatocalix[4]arene (5.2)

Same procedure as for 5.3, except solution is stirred for 60° C. for 3 hours. Workup affords grey powder 5.2 in 82% yield. Mp: >250° C. (dec). IR (KBr pellet): 3198s br, 1454s, 1280s, 1160s, 1037s, 883w, 847w, 808w, 786w, 626m, 567m, 542w, 408w. $^1$H NMR (300 MHz, D$_2$O): δ 8.03 (s, 2H), 7.60 (d, J=2.1 Hz, 2H), 7.53 (s, 2H), 6.16 (s, 2H), 4.25, 4.20 (2s, 2H), 3.86 (s, 2H), 3.65 (s, 4H). $^{13}$C NMR (75 MHz, D$_2$O): δ 151.4, 150.8, 147.7, 136.7, 136.5, 131.2, 128.9, 128.8, 128.4, 128.3, 127.2, 126.9, 126.5, 112.1, 30.6, 29.5. HR-ESI-MS: 766.9355 (MNa$^+$, C$_{28}$H$_{23}$BrO$_{13}$S$_3$Na$^+$; calcd 766.9365).

5-(4'-tolyl)sulfonamido-25,26,27,28-tetrahydroxy-11-17-23-trisulfonatocalix[4]arene (5.5)

5.4 (0.100 g, 0.147 mmol) and tosyl chloride (0.030 g, 1.1 eq, 0.162 mmol) are dissolved in 6 mL of 1M Na$_2$HPO$_4$/NaH$_2$PO$_4$ buffer (pH 8) and stirred overnight at room temperature. The aqueous solution is extracted with DCM (2×20 mL), EtOAc (1×25 mL), the aqueous phase is separated and evaporated. HPLC purification and evaporation of solvents in vacuo affords 43 mg of yellow powder in 45% yield. Mp: 196° C. (dec). IR (KBr pellet): 3467s br, 2952s, 2117w, 1454m, 1213s, 1155s, 1110s, 1037s, 900m, 783w, 746w, 651w, 620w, 601m, 559w. $^1$H NMR (300 MHz, D$_2$O): δ 7.71 (s, 2H), 7.69 (d, J=2.4 Hz, 2H), 7.53 (d, J=2.1 Hz, 2H), 6.95 (d, J=8.1 Hz, 2H), 6.80 (s, 2H), 6.12 (d, J=8.1 Hz, 2H), 4.03, 3.84 (br, 8H), 1.18 (s, 3H). $^{13}$C NMR (75 MHz, D$_2$O): δ 150.1, 149.9, 144.6, 144.1, 135.9, 135.8, 130.3, 130.0, 127.8, 127.71 (×2), 127.67, 127.5, 126.4, 126.1, 126.0, 125.8, 122.2, 30.1, 29.9, 19.5. HR-ESI-MS: 856.0473 (MNa$^+$, C$_{35}$H$_{31}$NO$_{15}$S$_4$Na$^+$; calcd 856.0474.)

5-(4'-carboxyphenyl)sulfonamido-25,26,27,28-tetrahydroxy-11-17-23-trisulfonatocalix[4]arene (5.6)

Prepared in the same manner as 5.5 except using 4-chlorosulfonyl benzoic acid (1.1 equiv.). After HPLC purification and evaporation of solvents in vacuo an off-white powder in 34% yield is obtained. Mp: 204° C. (dec). IR (KBr pellet): 3210s br, 1714s, 1474s, 1454s, 1401w, 1160s, 1110s, 1040s, 886w, 786w, 690w, 651m, 623m, 559w. $^1$H NMR (300 MHz, D$_2$O): δ 7.52 (s, 2H), 7.47 (d, J=1.8 Hz, 2H), 7.38 (d, J=1.8 Hz, 2H), 7.32 (s, 4H), 6.70 (s, 2H), 3.77, 3.64 (br, 8H). $^{13}$C NMR (75 MHz, D$_2$O): δ 166.7, 150.8, 150.6, 145.5, 139.7, 136.1, 135.6, 133.1, 130.1, 129.8, 128.7, 128.2, 127.8, 127.7, 127.1, 126.8, 126.6, 126.1, 122.4, 30.5, 30.4. HR-ESI-MS: 886.0216 (MNa$^+$, C$_{35}$H$_{29}$NO$_{17}$S$_4$Na$^+$; calcd 886.0216).

5-phenyl-25,26,27,28-tetrahydroxy-11-17-23-trisulfonatocalix[4]arene (5.8)

5.2 (0.042 g, 0.057 mmol), phenylboronic acid (0.0071 g, 1 equiv., 0.058 mmol), tetrabutyl ammonium bromide (0.0095 g, 0.5 equiv., 0.003 mmol), Pd(OAc)$_2$ (0.0028 g, 20 mol %) and sodium carbonate (0.0023 g, 3.8 equiv., 0.218 mmol) are dissolved in 5 mL of deionized H$_2$O inside a microwave vial and irradiated in the manner mentioned above. The aqueous solution is extracted with DCM (2×20 mL), EtOAc (1×25 mL), the aqueous phase is separated and evaporated. HPLC purification and evaporation of solvents in vacuo affords an off-white powder in 50% yield. Mp: >250° C. (dec). IR (KBr pellet): 3252s br, 1455s, 1216s, 1149, 1114, 1041, 783w, 761w, 654, 623m, 551m. $^1$H NMR (300 MHz, D$_2$O): δ 7.80 (s, 2H), 7.72 (s, 2H), 7.47 (s, 2H), 6.78 (s, 2H), 6.23 (d, J=7.5 Hz, 2H), 4.98 (s, 2H), 3.91 (br, 8H), 3.76 (br, 1H). $^{13}$C NMR (75 MHz, D$_2$O): δ 152.4, 150.4, 146.3, 136.7, 136.2, 136.1, 133.3, 128.6, 128.6, 128.1, 127.1, 127.0 (×2), 126.5, 126.3, 124.9 (×2), 124.8, 30.7, 30.5. HR-ESI-MS: 763.0587 (MNa$^+$, C$_{34}$H$_{28}$O$_{13}$S$_3$Na$^+$; calcd 763.0590).

5-(4'-cyanophenyl)-25,26,27,28-tetrahydroxy-11-17-23-trisulfonatocalix[4]arene (5.9)

Same procedure as for 5.8, except 4-cyanophenyl boronic acid (1 equiv.) is used. HPLC purification and evaporation of solvents in vacuo affords an off-white powder in 29% yield. Mp: >250° C. (dec). IR (KBr pellet): 3300s br, 2224m, 1602m, 1457s, 1211s, 1158s, 1110s, 1041s, 889w, 836w, 786w, 657w, 627m, 548w. $^1$HNMR (300 MHz, D$_2$O): δ 7.54 (m, 4H), 7.52 (m, 2H), 7.50 (m, 2H), 7.46 (m, 2H), 7.36 (m, 2H), 7.21 (s, 2H), 3.67, 3.64 (br, 8H). $^{13}$C NMR (75 MHz, D$_2$O): δ 151.5, 151.0, 148.9, 144.2, 136.2, 136.1, 133.2, 132.7, 128.2, 128.14, 128.10, 128.0, 126.9, 126.6 (×2), 126.5, 119.9, 118.1, 108.9, 31.0, 30.5. HR-ESI-MS: 788.0539 (MNa$^+$, C$_{35}$H$_{27}$NO$_{13}$S$_3$Na$^+$; calcd 788.0542).

5-(4'-carboxamidophenyl)-25,26,27,28-tetrahydroxy-11-17-23-trisulfonatocalix[4]arene (5.10)

5.10 is collected by HPLC and evaporation of solvents in vacuo as a partial hydrolysis product that occurs during the synthesis of 5.9 as an off-white powder in 26% yield. Mp: >250° C. (dec). IR (KBr pellet): 3246s br, 1607m, 1471m, 1455m, 1211s, 1152s, 1113s, 1040s, 786w, 654w, 627m, 551w. $^1$H (300 MHz, D$_2$O): δ 7.68 (d, J=8.4 Hz, 2H), 7.61 (m, 2H), 7.58 (d, J=2.1 Hz, 2H), 7.50 (s, 2H), 7.44 (d, J=8.4 Hz, 2H), 7.27 (s, 2H), 3.93 (s, 8H). $^{13}$C NMR (75 MHz, D$_2$O): δ 170.5, 149.7, 149.0, 146.5, 141.6, 134.3, 134.0, 131.9, 128.4, 126.3, 126.3, 126.13, 126.10, 126.0, 124.7, 124.6, 124.5 (×2), 28.9, 28.5. HR-ESI-MS: 784.0827 (MH$^+$, C$_{35}$H$_{29}$NO$_{14}$S$_3$H$^+$; calcd 784.0829).

5-(4'-carboxyphenyl)-25,26,27,28-tetrahydroxy-11-17-23-trisulfonatocalix[4]arene (5.11)

Same procedure as for 5.8, except 4-boronobenzoic acid (1 equiv.) is used. HPLC purification and evaporation of solvents in vacuo affords an off-white powder in 38% yield. Mp: >250° C. (dec). IR (KBr pellet): 3424s br, 1701m, 1608m, 1477m, 1458m, 1453m, 1186s, 1115s, 1045s, 892w, 856w, 777w, 677w, 660m, 627m, 553m, 517w. $^1$H NMR (300 MHz, D$_2$O): δ 8.06 (d, J=8.4 Hz, 2H), 7.72 (d, J=2.1 Hz, 2H), 7.70 (d, J=2.4 Hz, 2H), 7.68 (d, J=8.4 Hz, 2H), 7.59 (s, 2H), 7.55 (s, 2H), 4.38, 4.37 (2s, 8H). $^{13}$C NMR (75 MHz, D$_2$O): δ 170.6, 152.1, 151.4, 149.0, 144.8, 136.4, 136.1, 133.9, 130.4, 128.8, 128.6, 128.6, 128.5, 128.2, 127.9, 126.8, 126.8, 126.7, 126.7, 31.2, 30.8. HR-ESI-MS: 807.0488 (MNa$^+$, C$_{35}$H$_{28}$O$_{15}$S$_3$Na$^+$; calcd 807.0488).

5-(4'-aminomethylphenyl)-25,26,27,28-tetrahydroxy-11-17-23-trisulfonatocalix[4]arene (5.12)

Same procedure as for 5.8, except 4-aminomethylbenzeneboronic acid hydrochloride (1 equiv.) is used. HPLC purification and evaporation of solvents in vacuo affords an off-white powder in 32% yield. MP>250° C. (dec). IR (KBr pellet): 3236br, 2950br, 1474m, 1211m, 1161m, 1113m, 1040s, 657w, 628w, 553w. $^1$H NMR (300 MHz, D$_2$O): δ 7.86 (d, J=2.0 Hz, 2H), 7.78 (d, J=2.0 Hz, 2H), 7.56 (s, 2H), 7.11 (s, 2H), 6.65 (d, J=8.9 Hz, 2H), 6.03 (d, J=7.4 Hz, 2H), 4.12 (br, 8H), 2.58 (s, 2H) $^{13}$C NMR (75 MHz, D$_2$O): 152.5, 150.9, 147.5, 138.9, 136.4, 135.9, 133.4, 130.0, 128.8, 128.7, 128.4, 128.0, 127.9, 127.4, 126.5 (×2), 126.4 (×2), 41.9, 30.9, 30.6. HR-ESI-MS: 770.1034 (MH$^+$, C$_{35}$H$_{32}$NO$_{13}$S$_3^+$; calcd 770.1036).

5-(2'-methylphenyl)-25,26,27,28-tetrahydroxy-11-17-23-trisulfonatocalix[4]arene (5.13)

40.9 mg of 5.2 (0.054 mmol), 10.6 mg 2-tolylboronic acid (1.3 eq), 5.2 mg palladium (II) acetate (40 mol %), and 23.4 mg sodium carbonate (3.8 eq) were dissolved in 5 mL of distilled H$_2$O in a microwave vial. Vial was capped and heated in a silicon oil bath at 150° C. for 5 minutes. Product was purified using reverse phase HPLC and lyophilized to produce an 18% yield of a fluffy white powder. $^1$H NMR (300 MHz, D$_2$O): δ 7.60 (s, 4H), 7.52 (s, 2H), 6.96 (s, 2H), 6.74 (d, J=7.2 Hz, 2H), 6.66 (d, J=7.0 Hz, 2H), 6.13-6.18 (m, 2H), 3.98-4.01 (m, 8H), 1.66 (s, 3H). $^{13}$C NMR (75 MHz, D$_2$O): δ152.2, 146.8, 136.3, 135.6, 129.9, 128.9, 128.0, 127.5, 126.6, 126.4, 126.3, 125.2, 30.5, 30.3, 19.3 HR-ESI-MS: 753.07629 (C$_{35}$H$_{29}$O$_{13}$S$_3^-$ calc. 753.0776).

5-(2',6'-dimethylphenyl)-25,26,27,28-tetrahydroxy-11-17-23-trisulfonatocalix[4]arene (5.14)

Same procedure as for 5.13, using 2,6-dimethylphenylboronic acid. Following reverse phase HPLC a fluffy white powder was isolated with a 26% yield. $^1$H NMR (300 MHz, D$_2$O): δ 7.66 (s, 2H), 7.62 (s, 2H), 7.55 (s, 2H), 7.05-7.08 (m, 1H), 6.98-6.99 (m, 2H), 6.67 (s, 2H), 3.98-3.99 (m, 8H), 1.44 (s, 6H). $^{13}$C NMR (75 MHz, D$_2$O): δ 153.3, 136.5, 134.7, 134.2, 129.6, 129.5, 128.5, 128.1, 127.1, 126.3, 126.0, 30.1, 19.2. HR-ESI-MS: 767.09716. (C$_{36}$H$_{31}$O$_{13}$S$_3^-$, calc. 767.0932)

5-(2'-methoxyphenyl)-25,26,27,28-tetrahydroxy-11-17-23-trisulfonatocalix[4]arene (5.15)

Same procedure as for 5.13, using 2-methoxyphenylboronic acid, and heating for 20 minutes. Following reverse phase HPLC a beige powder was isolated with a 19% yield. $^1$H NMR (300 MHz, D$_2$O): δ7.48-7.52 (m, 6H), 7.17-7.18 (m, 3H), 6.83 (s, 1H), 6.69 (s, 2H), 6.38 (s, 3H), 3.90 (s, 8H), 3.42 (s, 3H). $^{13}$C NMR (75 MHz, D$_2$O): δ 155.5, 151.2, 151.0, 147.1, 139.0, 136.5, 135.4, 132.2, 130.2, 129.9, 128.7, 128.4, 128.3, 127.2, 126.5, 124.6, 120.8, 111.8, 55.0, 30.7, 30.4. HR-ESI-MS: 769.07078. (MNa$^+$C$_{35}$H$_{29}$O$_{14}$S$_3^-$, calc. 769.0725)

5-(2'-chlorophenyl)-25,26,27,28-tetrahydroxy-11-17-23-trisulfonatocalix[4]arene (5.16)

Same procedure as for 5.13, using 2-chlorophenylboronic acid, and heating for 15 minutes. Following reverse phase HPLC a light brown powder was isolated with a 17% yield. $^1$H NMR (300 MHz, D$_2$O): δ 7.65 (s, 2H), 7.49 (s, 4H), 7.19 (s, 2H), 6.64 (m, 1H), 6.37 (s, 1H), 5.11-5.24 (m, 2H), 4.02-4.06 (m, 2H). $^{13}$C NMR (125 MHz, D$_2$O): δ135.9, 130.5, 129.6, 129.3, 128.9, 126.8 126.5, 31.3, 30.8. HR-ESI-MS: 773.02134. (C$_{34}$H$_{26}$ClO$_{13}$S$_3^-$, calc. 773.0230).

5-(2'-formylphenyl)-25,26,27,28-tetrahydroxy-11-17-23-trisulfonatocalix[4]arene (5.17)

Same procedure as for 5.13, using 2-formylphenylboronic acid, and heating for 1 hour. Following reverse phase HPLC a pale yellow powder was isolated with a 37% yield. $^1$H NMR (300 MHz, D$_2$O): δ7.64-7.70 (m, 5H), 7.45 (s, 3H), 7.00 (s, 2H), 6.25 (s, 1H), 5.85 (s, 1H), 3.92-4.02 (m, 8H). $^{13}$C NMR (75 MHz, D$_2$O): δ152.2, 128.7, 128.6, 128.1, 127.4, 126.8, 126.3, 30.6, 30.4. ESI-MS: 767.8 (C$_{35}$H$_{27}$O$_{14}$S$_3^-$, calc. 767.05).

5-(2'-hydroxymethylphenyl)-25,26,27,28-tetrahydroxy-11-17-23-trisulfonatocalix[4]arene (5.18)

Same procedure as for 5.13, using 2-(hydroxymethyl)phenylboronic acid, and heating for 1 hour. Following reverse phase HPLC a white powder was isolated with a 18% yield. $^1$H NMR (300 MHz, D$_2$O): δ7.43-7.85 (m, 10H), 7.02 (m, 2H), 3.84-4.03 (m, 10H). $^{13}$C NMR (75 MHz, D$_2$O): 129.9, 128.1, 127.1, 126.9, 126.7, 126.4, 30.3. ESI-MS: 769.3. (C$_{35}$H$_{29}$O$_{14}$S$_3^-$, calc. 769.07)

5-(2'-fluorophenyl)-25,26,27,28-tetrahydroxy-11-17-23-trisulfonatocalix[4]arene (5.19)

Same procedure as for 5.13, using 2-fluorophenylboronic acid, and heating for 1 hour. Following reverse phase HPLC a white powder was isolated with a 17% yield. $^1$H NMR (300 MHz, D$_2$O): δ8.87 (s, 1H), 7.47-8.09 (m, 9H), 6.71-7.05 (m, 2H), 6.30 (s, 1H), 4.10 (m, 8H). (75 MHz, D$_2$O): 212.0, 131.5, 131.0, 128.8, 128.5, 128.1, 126.8, 126.5, 30.7, 30.3. ESI-MS: 757.3 (C$_{34}$H$_{26}$FO$_{13}$S$_3^-$, calc. 757.05).

General Protocol for Macrocyclic Sensors with Dye Covalently Bound Via Amine-Isothiocyanate Reactions.

Starting material amino-calixarene (5.4 or 5.12) and isothiocyanate dye are dissolved in a 2 mL mixture of pyridine and DMF (1:1) and stirred overnight at room temperature in the dark. The reaction mixture is poured into 15 mL of $H_2O$ and extracted with 2×20 mL $CH_2Cl_2$, 1×15 mL EtOAc and the aqueous layer is lyophilized to dryness in the dark. The crude product is thus obtained is purified by HPLC. Yield of fluorescein derivative (6.0): 13% HR-ESIMS: calc: 1067.0768 found: 1067.0769 $[M-H]^-$. Yield of tetramethylrhodamine derivative (6.1), mixture of 5 and 6 isomers): 15% ESIMS: calc: 1123.19 found: 1124.1 $[M+H]^+$. Yield of fluorescein derivative (6.2): 10% HR-ESIMS: calc: 1157.1 found: 1157.3 $[M-H]^-$. Yield of tetramethylrhodamine derivative (6.3), mixture of 5 and 6 isomers): 12% ESIMS: calc: 1214.2 found: 1213.9 $[M+H]^+$.

Arrays

All examples include (1) a set of post-translationally modified analytes that is to be characterized, (2) a set of macrocyclic sensors (the macrocyclic sensor array) that is used to generate a pattern of optical responses, (3) an exemplary set of optical responses in the form of raw data for multiple replicates of the determination, (4) a presentation of the same raw data that has been processed by principal component analysis (PCA), and (5) a statistical method for reducing complex data sets into two-dimensional plots.

General Protocol:

Stock solutions were prepared of the peptides to be discriminated, in this example different peptides all bearing trimethyllysine in different sequence contexts: H3K4me3=$NH_3$-ARTK(me3)QTAY-$NH_2$, H3K9me3=Ac-TARK(me3)STGY-$NH_2$, H3K27me3=Ac-AARKSAPY-$NH_2$, H3K36me3=Ac-GGVK(me3)KPHY-$NH_2$, H4K20me3=Ac-RHRK(me3)VLRY-$NH_2$. Stock solutions of dye lucigenin, Hosts (PSC4 and PSC(Br)), and buffer were also prepared as tabulated in Table 2.

TABLE 2

Stock solutions used in typical data collection procedure with initial and final concentrations, volumes used, and dilutions in an experimental set-up.

| | Experimental Well types | | |
|---|---|---|---|
| Stock Solution of Reagent | Blank | $F_0$ | Analytes |
| | Volume of stock solution added per well (µL) | | |
| 5 µM LCG | 20 | 20 | 20 |
| 0.2M $Na_2HPO_4$/$NaH_2PO_4$ buffer [pH = 7.4] | 10 | 10 | 10 |
| 15 µM Host (PSC4 or PSC(Br)) | — | 20 | 20 |
| 50 µM Peptide | — | — | 20 |
| $H_2O$ | 170 | 150 | 130 |
| Total Volume per well (µL) | 200 | 200 | 200 |
| Reagent | Final concentrations of reagents per well | | |
| LCG | 0.5 µM | 0.5 µM | 0.5 µM |
| $Na_2HPO_4$/$NaH_2PO_4$ buffer [pH = 7.4] | 10 mM | 10 mM | 10 mM |

TABLE 2-continued

Stock solutions used in typical data collection procedure with initial and final concentrations, volumes used, and dilutions in an experimental set-up.

| | Experimental Well types | | |
|---|---|---|---|
| | Blank | $F_0$ | Analytes |
| Host (PSC4 or PSC(Br)) | — | 1.5 µM | 1.5 µM |
| Peptide | — | — | 5 µM |

Where the analytes in this example are:
$A_1$ = H3K4me3
$A_2$ = H3K9me3
$A_3$ = H3K27me3
$A_4$ = H3K36me3
$A_5$ = H4K20me3

Two series of samples were created, one for each sensor element, where the macrocyclic compound in used in one plate was PSC4 and the macrocyclic compound used in the second was PSC(Br). Each of these two series was created in a 96-well plate for ease of acquisition and preparation. In each 96-well plate there were six replicates of each well type: Blank, $F_0$, $A_1$, $A_2$, $A_3$, $A_4$, and $A_5$, as described in Table 2, Each well type is mixed and diluted to a final volume of 200 uL in a 96-well plate as indicated in Table 2.

Fluorescence emission data for each 96-well plate are acquired using a microplate reader, with excitation at the dye's absorbance maximum of 369 nm and emission monitored at the dye's emission maximum of 505 nm. Emission from $A_1$, $A_2$, $A_3$, $A_4$, and $A_5$ for each sensor generated fluorescent responses F. Emission intensities for each analyte sample (F) are subtracted from initial fluorescence intensities for each sample prior to addition of analyte ($F_0$) producing $F-F_0$ values used in subsequent analyses. In the current example, $F-F_0$ values for the two sensors were subjected to principle component analysis to produce two principle components that were plotted on an X-Y scatter plot to generate the 2D PCA analyte map.

FIGS. 12a and 12b collectively illustrate the ability of the disclosed method and sensors to discriminate a single peptide sequence on the basis of degree of post-translational methylation. FIG. 12a is a bar graph illustrating exemplary patterns of fluorescence data obtained in the exemplary embodiment. With reference to FIGS. 12a and 12b, the analytes examined include H3K36=peptide Ac-GGVK-KPHY-$NH_2$, H3K36me=peptide H3K36 where lysine 36 is monomethylated, H3K36me2=peptide H3K36 where lysine 36 is dimethylated, and H3K36me3=peptide H3K36 where lysine 36 is trimethylated, and the macrocyclic sensor array components include Sensors S1 (white)=1.5 uM PSC4, 500 nm LCG in 10 mM phosphate buffer (pH=7.4), and S3 (black)=1.5 uM PSC(Br), 500 nm LCG in 10 mM phosphate buffer (pH=7.4). FIG. 12b is a plot obtained using linear discriminant analysis of replicated fluorescence data that illustrates the ability to differentiate analytes by pattern recognition.

Figure 13B:
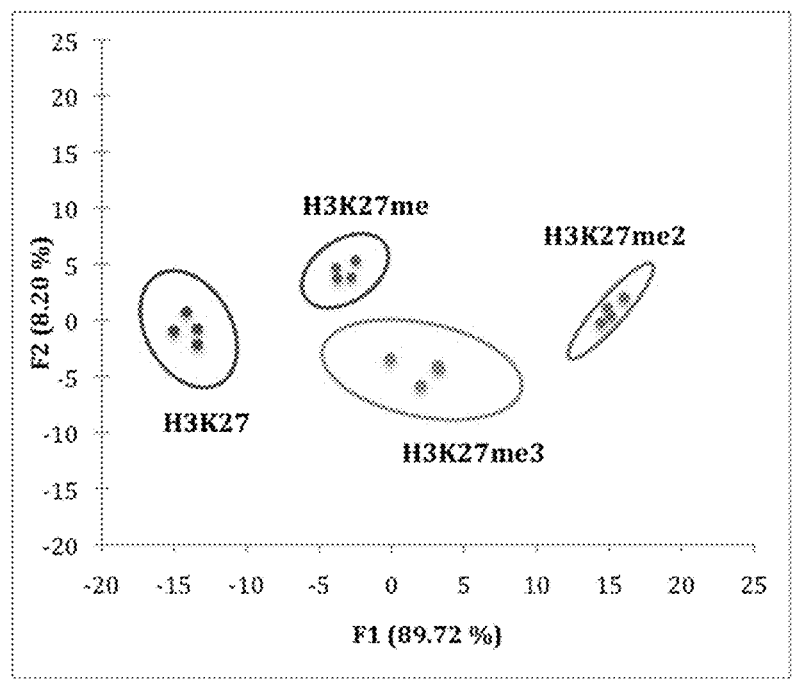

FIGS. 13a and 13b collectively illustrate the ability of the disclosed method and sensors to discriminate a single peptide sequence on the basis of degree of post-translational methylation, and demonstrate selectively higher responses to lower states of methylation (in this case dimethyllysine). FIG. 13a is a bar graph illustrating exemplary patterns of fluorescence data obtained in the exemplary embodiment. With reference to FIGS. 13a and 13b, the analytes examined include H3K27=peptide Ac-AARKSAPY-$NH_2$, H3K27me=peptide H3K27 where lysine 27 is monomethylated, H3K27me2=peptide H3K27 where lysine 27 is dimethylated, and H3K27me3=peptide H3K27 where lysine 27 is trimethylated, and the macrocyclic sensor array components include Sensors 7-13 consisting of: 500 nM LCG in 10 mM phosphate buffer (pH=7.4), each containing a different macrocyclic host as depicted in FIG. 7b. FIG. 13b is a plot obtained using linear discriminant analysis of replicated fluorescence data that illustrates the ability to differentiate analytes by pattern recognition.

Figure 14A:
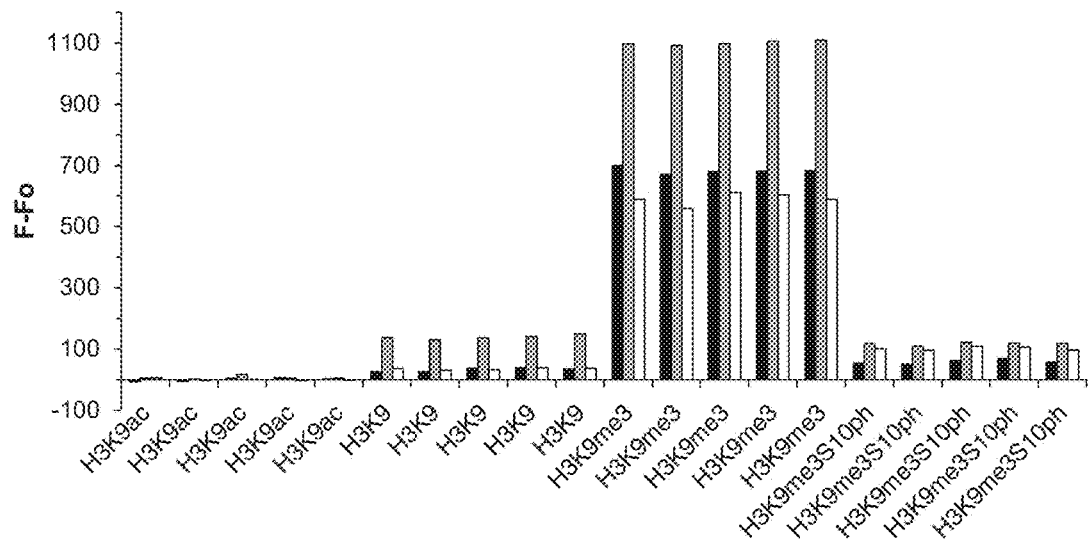
FIGS. 14a and 14b collectively illustrate the ability of the disclosed array and sensor to discriminate closely related analytes on the basis of combinations of different PTMs.
Figure 14B:
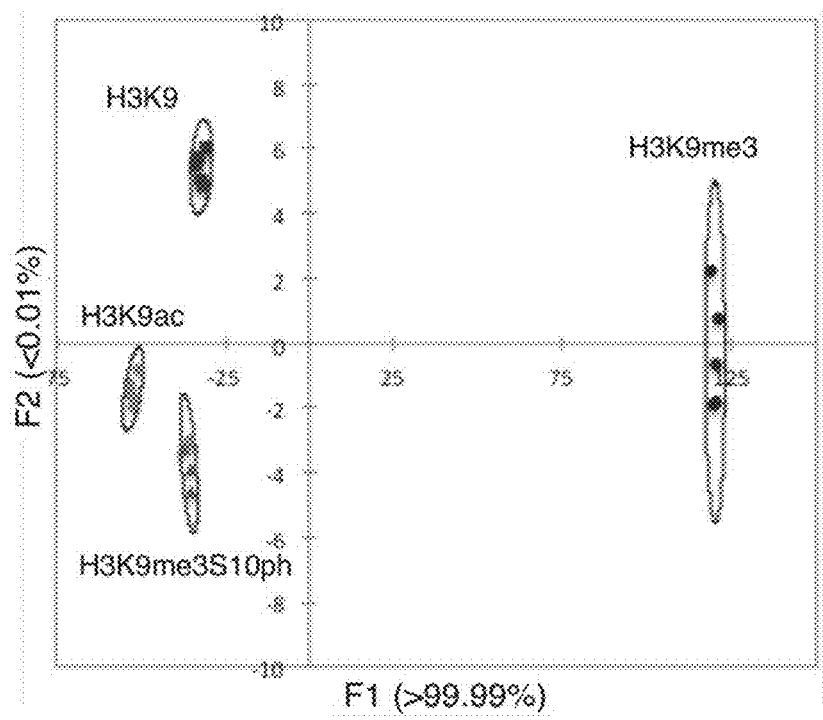

FIGS. 14a and 14b collectively illustrate the ability of the disclosed method and sensor to discriminate closely related analytes on the basis of combinations of different PTMs. FIG. 14a is a bar graph illustrating exemplary patterns of fluorescence data obtained in the exemplary embodiment. With specific reference to FIGS. 14a and 14b, the analytes examined include H3K9 (peptide Ac-TARKSTGY-NH$_2$), H3K9ac (H3K9 peptide acetylated at K), H3K9me3 (H3K9 peptide trimethylated at K), H3K9me3S10ph (H3K9 peptide trimethylated at K and phosphorylated at S). The macrocyclic sensor array components include S1 (illustrated as the black bars in FIG. 14a, conditions=1.5 µM PSC4, 500 nM LCG in 10 mM phosphate buffer [pH=7.4]), S2 (illustrated as the gray bars in FIG. 14a, conditions=1.5 µM PSC6, 500 nM LCG in 10 mM phosphate buffer [pH=7.4]), and S5 (illustrated as the white bars in FIG. 14a, conditions=1.5 µM PSC4, 500 nM LCG in 10 mM NH$_4$OAc [pH=4.8]). FIG. 14b is a plot obtained using linear discriminant analysis of replicated fluorescence data that illustrates the ability to differentiate analytes by pattern recognition.

Figure 15A:
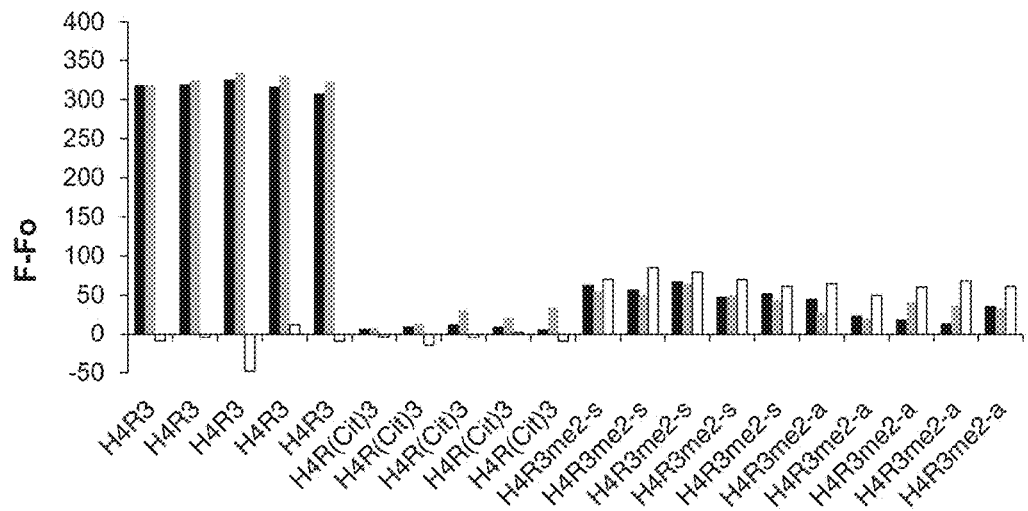
FIGS. 15a and 15b collectively illustrate the ability of the disclosed array and sensor to discriminate closely related analytes on the basis of isomeric PTMs.
Figure 15B:
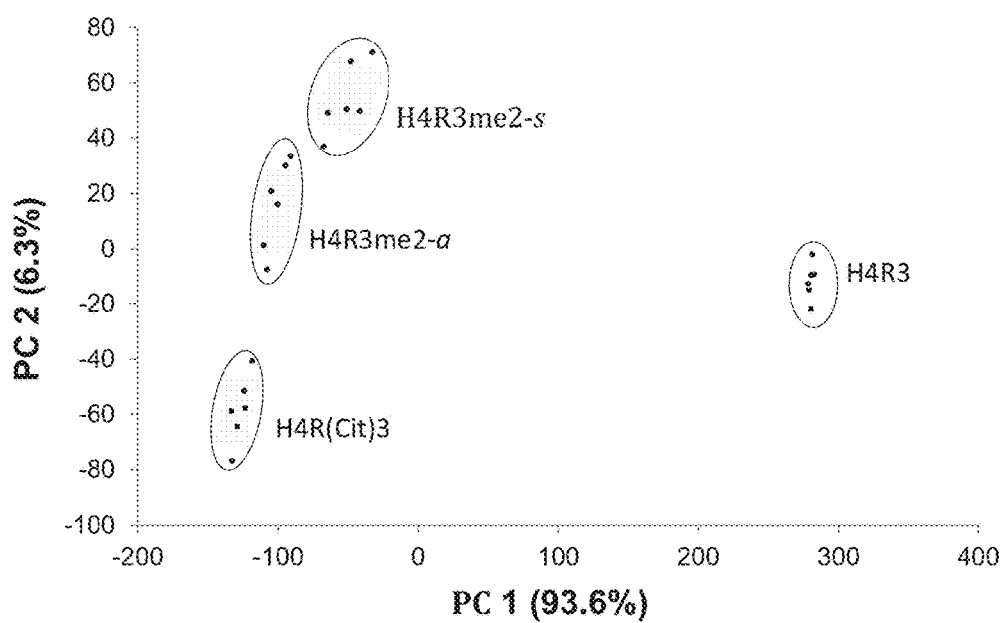

FIGS. 15a and 15b collectively illustrate the ability of the disclosed method and sensor to discriminate closely related analytes on the basis of isomeric PTMs. FIG. 15a is a bar graph illustrating exemplary patterns of fluorescence data obtained in the exemplary embodiment. With reference to FIGS. 15a and 15b, the analytes examined include H4R3 (peptide NH$_2$-SGRGKGGY-NH$_2$), H4R(Cit)$_3$ (H4R3 citrullinated at R), H4R3me2-s (peptide H4R3 symmetrically dimethylated at R), and H4R3me2-a (peptide H4R3 asymmetrically dimethylated at R). The macrocyclic sensor array components include S1 (illustrated as the black bars in FIG. 15a, conditions=1.5 µM PSC4, 500 nM LCG in 10 mM phosphate buffer [pH=7.4]), S2 (illustrated as the gray bars in FIG. 15a, conditions=1.5 µM PSC6, 500 nM LCG in 10 mM phosphate buffer [pH=7.4]), and S5 (illustrated as the white bars in FIG. 9a, conditions=1.5 µM PSC(Br), 500 nM LCG in 10 mM phosphate buffer [pH=7.4]). FIG. 15b is a plot obtained using principal component analysis of replicated fluorescence data that illustrates the ability to differentiate analytes by pattern recognition.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A macrocyclic compound having a formula

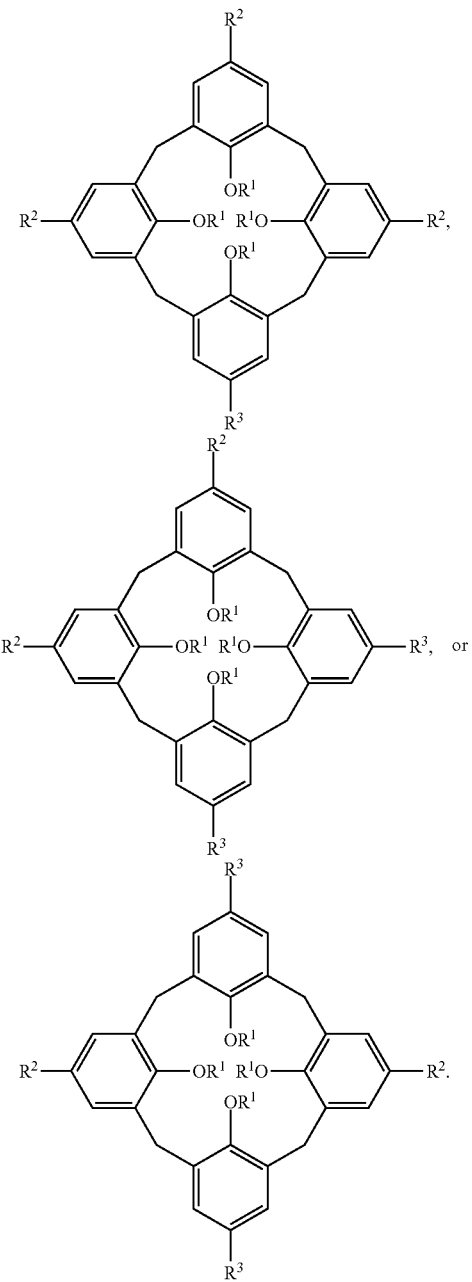

wherein $R^1$ is H, $R^2$ is selected from SO$_3$H, CO$_2$H, and PO$_3$H$_2$, and $R^3$ is heteroaryl, aryl, amine, or combinations thereof.

2. The macrocyclic compound of claim 1, wherein $R^3$ is NH$_2$, NHR$^a$, NR$^a$R$^b$, or (NR$^a$R$^b$R$^c$)$^+$, where R$^a$, R$^b$ and R$^c$ independently are selected from aryl, —C(S)NHaryl or —SO$_2$aryl, where the —C(S)NHaryl or —SO$_2$aryl group is optionally substituted with one or more functional groups selected from cyano, amide, carboxyl, carboxylic acid, amine, alkyl amine, C$_1$-C$_{10}$alkyl, C$_1$-C$_{10}$alkoxy, halo, aldehyde, hydroxyl, C$_1$-C$_{10}$alkylhydroxyl, or combinations thereof.

3. An array, comprising at least two macrocyclic sensors, wherein at least one macrocyclic sensor comprises a macrocyclic compound having a formula selected from

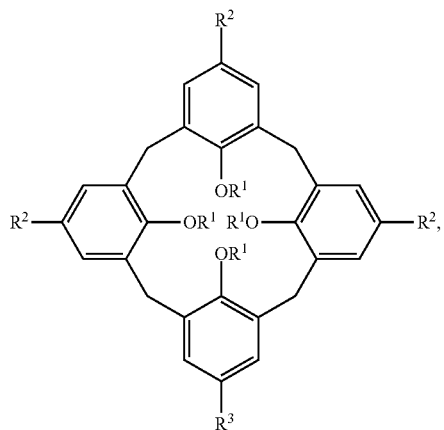

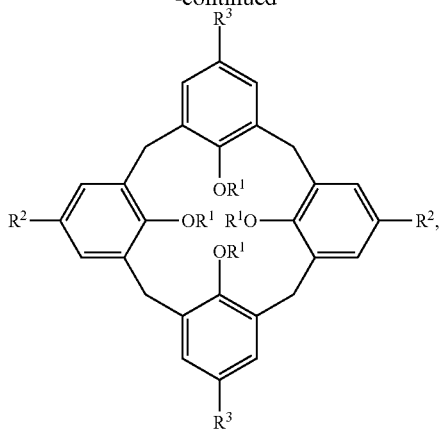

or an anionic form thereof in an aqueous environment, wherein:
$R^1$ is H;
each $R^2$ is independently selected from $SO_3H$, $CO_2H$, or $PO_3H_2$; and
$R^3$ is heteroaryl, aryl, amine, or combinations thereof.

4. The array of claim 3, wherein the macrocyclic compound has a formula

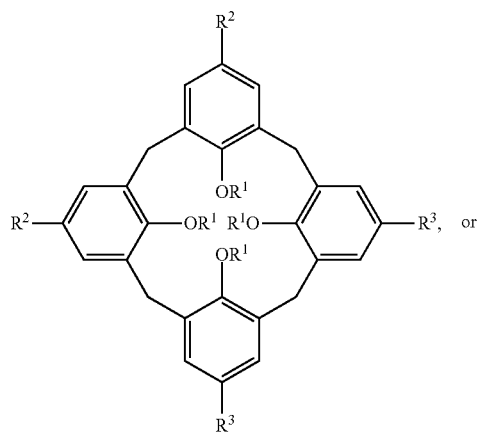, or

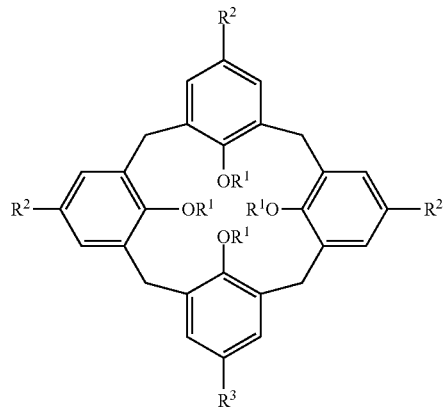

5. The array of claim 4, wherein the anionic form of the macrocyclic compound in the aqueous environment is

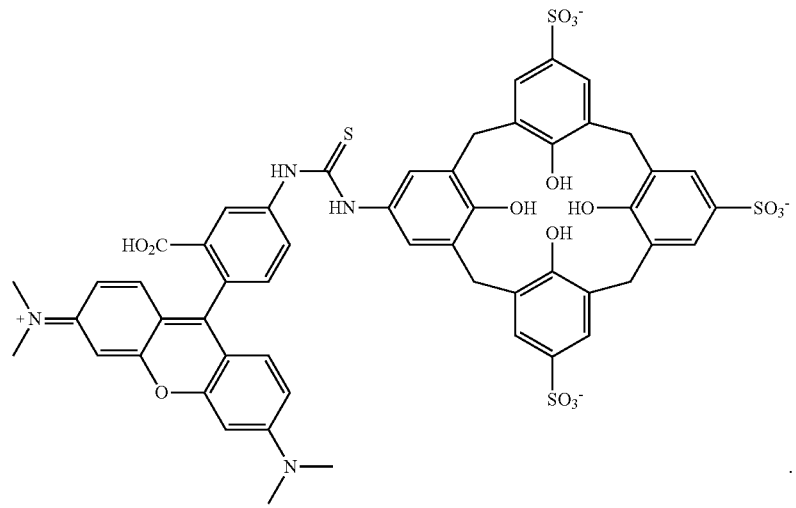

6. The array of claim 4, wherein the anionic form of the macrocyclic compound in the aqueous environment is

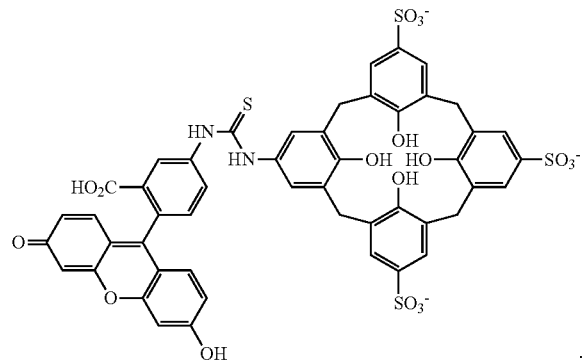

7. The array of claim 4, wherein the anionic form of the macrocyclic compound in the aqueous environment is

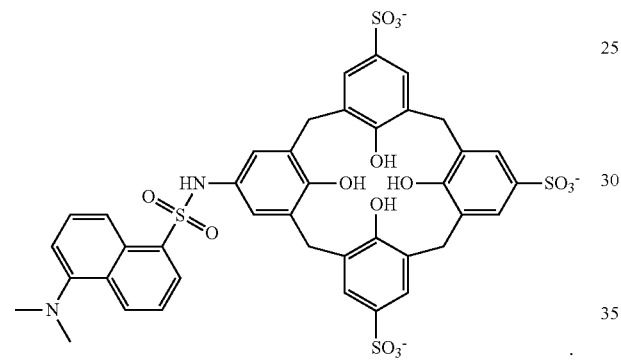

8. The array of claim 3, wherein the sensor comprises a detectable moiety capable of producing a signal by fluorescence or absorbance.

9. The array of claim 8, wherein the detectable moiety is a dye selected from a lucigenin, a fluorescein, a naphthalene-based dye, a pyrene-based dye, or an azole.

10. The array of claim 8, wherein the detectable moiety is a dye selected from fluorescein, fluorescein isothiocyanate, rhodamine, tetramethyl rhodamine isothiocyanate (TRITC), naphthalimide, 4-dimethylaminonaphthalimide (4-DMN), coumarin, cyanine, dansyl, PSP, thiazole orange, Oregon green, eosin, Texas red, Cal Fluor, indocarbocyanine, oxacarbocyanine, thiacarbocyanine, merocyanine, Quasar dyes, prodan derivatives, pyridyloxazole, nitrobenzoxadiazole, benzoxadiazole, cascade blue, Nile red, Nile blue, cresyl violet, oxazine 170, proflavin, acridine orange, acridine yellow, auramine, crystal violet, malachite green, porphyrin, phtalocyanine, or bilirubin.

11. The array of claim 8, wherein the macrocyclic compound is covalently coupled to the detectable moiety.

12. The array of claim 8, wherein the macrocyclic compound is non-covalently coupled to the detectable moiety.

13. The array of claim 3, wherein the array is for identifying, or identifying and quantifying an analyte, wherein the analyte is a biological molecule selected from an amino acid, a peptide, or a protein.

14. The array of claim 13, wherein the analyte is a histone or histone-derived peptide sequence.

15. The array of claim 3, wherein the array is configured for detecting an analyte having at least one post-translational modification, wherein the post-translational modification results from phosphorylation, methylation, acetylation, citrullination, butyrylation, crotonylation, ubiquitination, proline cis-trans isomerization of the analyte, or combinations thereof.

16. The array of claim 13, wherein identifying the analyte comprises identifying members of a group of analytes comprising a single peptide or protein sequence bearing different post-translational modifications at a single site.

17. The array of claim 13, wherein identifying the analyte comprises identifying a particular peptide or protein sequence among a plurality of analytes that all comprise the same post-translational modification within different peptide or protein sequences.

18. A method, comprising:
exposing a sample comprising an analyte to a sensor comprising a macrocyclic compound having a formula selected from

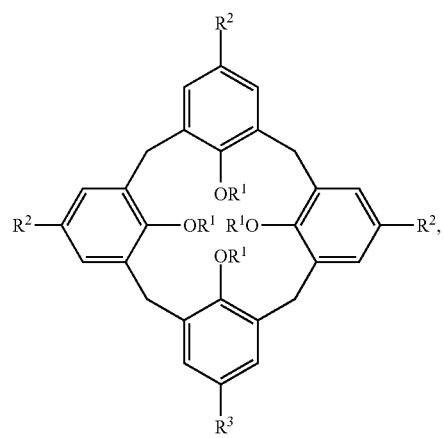

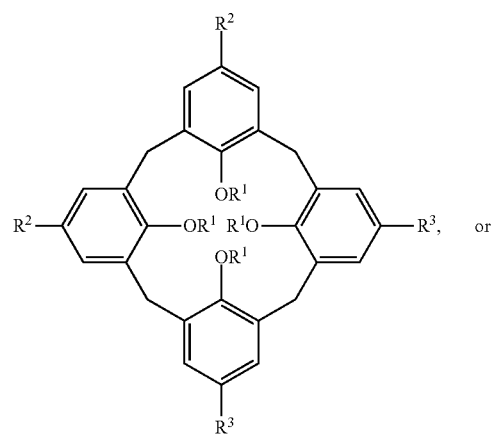

or

43

-continued

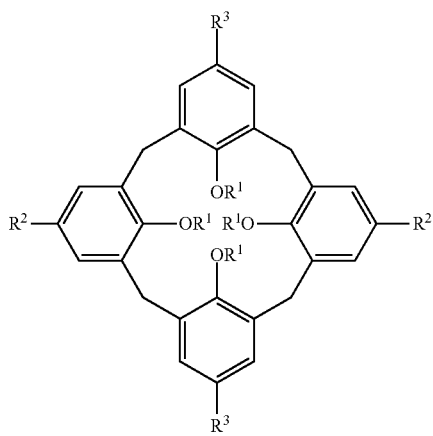

or an anionic form thereof in an aqueous environment, wherein $R^1$ is H; each $R^2$ is independently selected from $SO_3H$, $CO_2H$, or $PO_3H_2$; and each $R^3$ is independently selected from heteroaryl, aryl, amine, or combinations thereof; and detecting a signal produced by interaction between the analyte and the sensor.

19. The method of claim 18, further comprising quantifying the analyte.

20. The method of claim 18, wherein the analyte is a biological molecule selected from an amino acid, a peptide, and a protein comprising at least one post-translational modification.

21. The method of claim 18, wherein the analyte is a histone.

22. The method of claim 18, wherein the analyte has a post-translational modification resulting from phosphorylation, methylation, acetylation, citrullination, butyrylation, crotonylation, ubiquitination, Proline cis-trans isomerization, or combinations thereof.

23. The method of claim 18, wherein the signal is an optical signal detected using fluorescence or absorbance methods.

24. The method of claim 18, further comprising:
exposing the sample to an enzyme;
determining the progress of a reaction between the enzyme and the analyte; and
determining the identity of a product produced by the reaction.

44

25. A macrocyclic compound having a structure

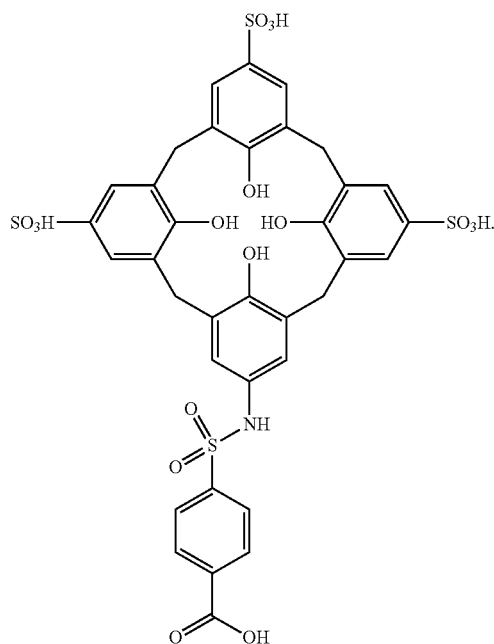 [SMILES: O=C(O)c1ccc(S(=O)(=O)Nc2cc3c(O)c(c2)Cc2cc(S(=O)(=O)O)cc(c2O)Cc2cc(S(=O)(=O)O)cc(c2O)Cc2cc(S(=O)(=O)O)cc(c2O)C3)cc1]

26. An array, comprising at least two macrocyclic sensors, wherein at least one macrocyclic sensor comprises the macrocyclic compound of claim 25, or an anionic form thereof in an aqueous environment.

27. A method, comprising:
exposing a sample comprising an analyte to a sensor comprising the macrocyclic compound of claim 25, or an anionic form thereof in an aqueous environment; and
detecting a signal produced by interaction between the at least one analyte and the sensor.

28. The macrocyclic compound of claim 1, wherein the macrocyclic compound is selected from:
5-amino-25, 26, 27, 28-tetrahydroxy-11-17-23-trisulfonatocalix[4]arene;
5-(4'-tolyl)sulfonamido-25, 26, 27, 28-tetrahydroxy-11-17-23-trisulfonatocalix[4]arene;
5-(4'-carboxyphenyl)sulfonamido-25, 26, 27, 28-tetrahydroxy-11-17-23-trisulfonatocalix[4]arene;
5-phenyl-25, 26, 27, 28-tetrahydroxy-11-17-23-trisulfonatocalix[4]arene;
5-(4'-cyanophenyl)-25, 26, 27, 28-tetrahydroxy-11-17-23-trisulfonatocalix[4]arene;
5-(4'-carboxamidophenyl)-25, 26, 27, 28-tetrahydroxy-11-17-23-trisulfonatocalix[4]arene;
5-(4'-carboxyphenyl)-25, 26, 27, 28-tetrahydroxy-11-17-23-trisulfonatocalix[4]arene;
5-(4'-aminomethylphenyl)-25, 26, 27, 28-tetrahydroxy-11-17-23-trisulfonatocalix[4]arene;
5-(2'-methylphenyl)-25, 26, 27, 28-tetrahydroxy-11-17-23-trisulfonatocalix[4]arene;
5-(2',6'-dimethylphenyl)-25, 26, 27, 28-tetrahydroxy-11-17-23-trisulfonatocalix[4]arene;
5-(2'-methoxyphenyl)-25, 26, 27, 28-tetrahydroxy-11-17-23-trisulfonatocalix[4]arene;
5-(2'-chlorophenyl)-25, 26, 27, 28-tetrahydroxy-11-17-23-trisulfonatocalix[4]arene;
5-(2'-formylphenyl)-25, 26, 27, 28-tetrahydroxy-11-17-23-trisulfonatocalix[4]arene;

5-(2'-hydroxymethylphenyl)-25, 26, 27, 28-tetrahydroxy-11-17-23-trisulfonatocalix[4]arene;
5-(2'-fluorophenyl)-25, 26, 27, 28-tetrahydroxy-11-17-23-trisulfonatocalix[4]arene;
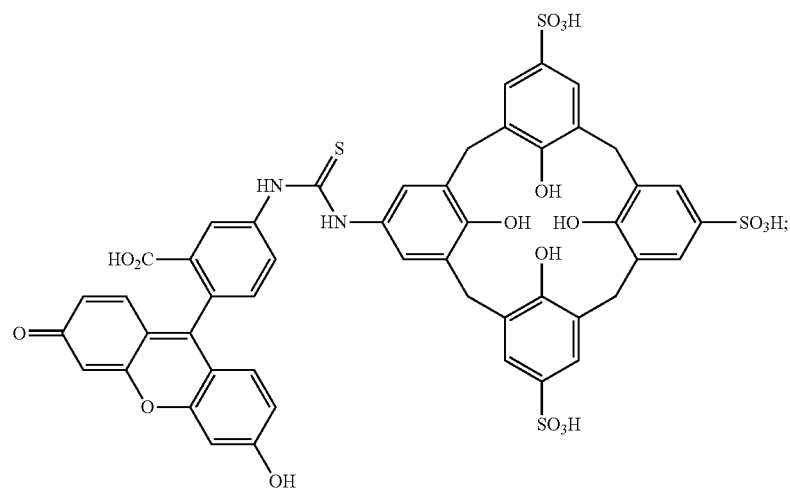
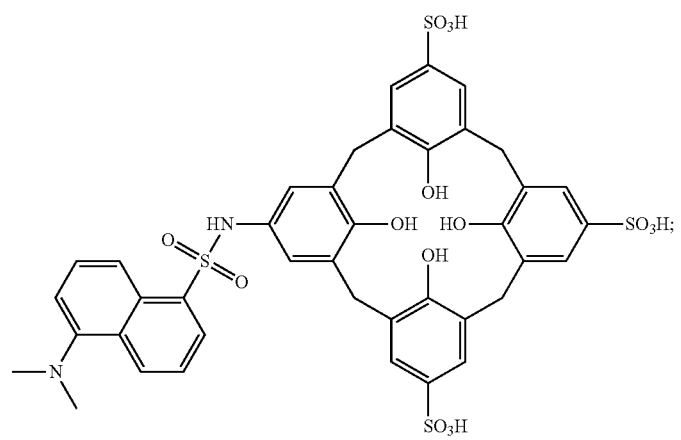
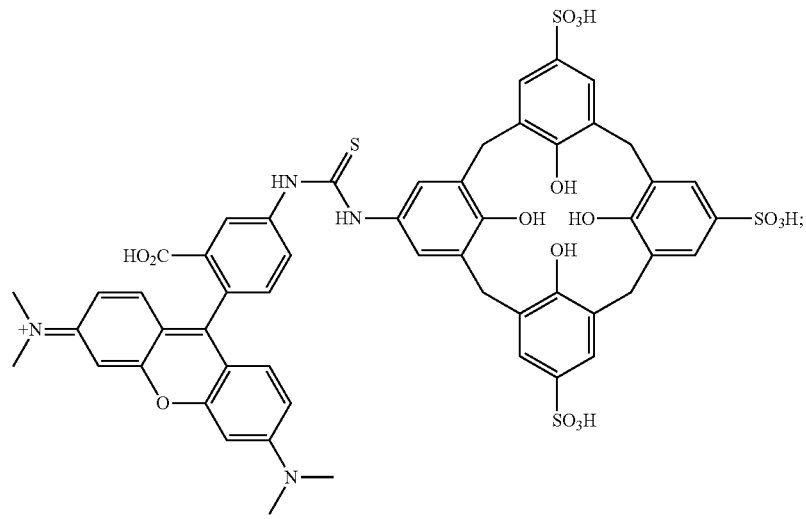

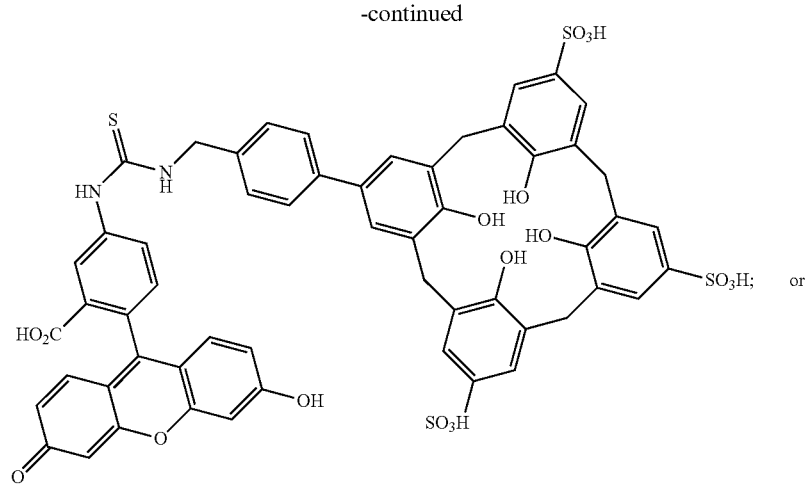
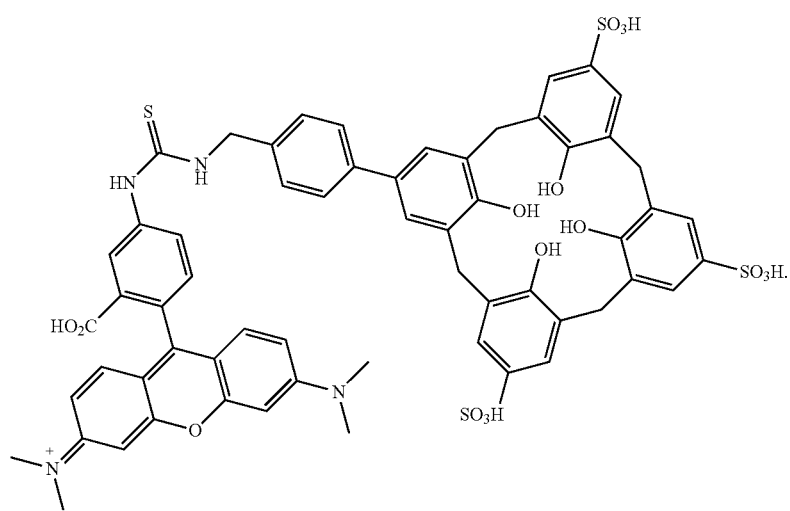
29. The compound of claim 1, wherein $R^3$ is $NH_2$,
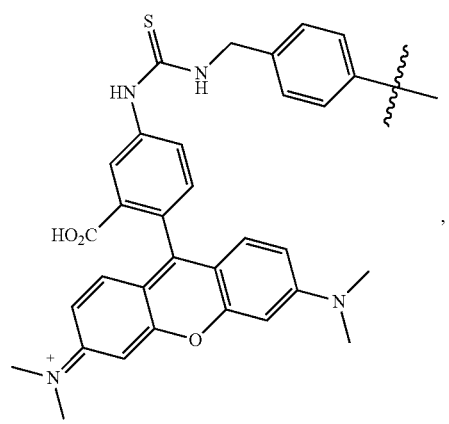
-continued
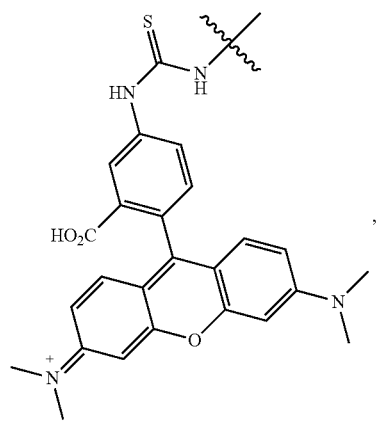

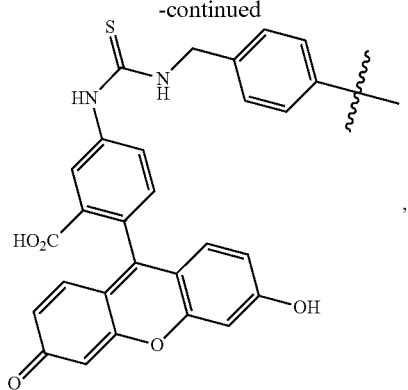,

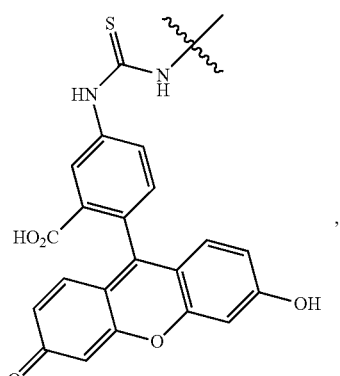,

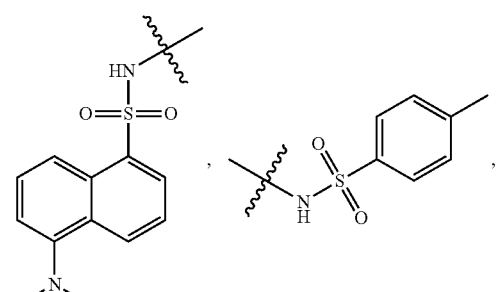

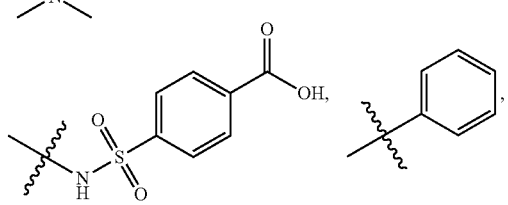

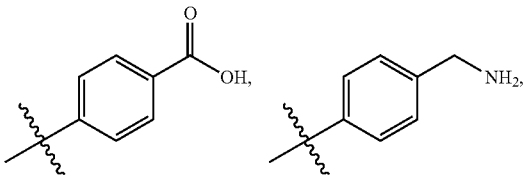

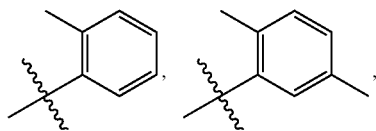,

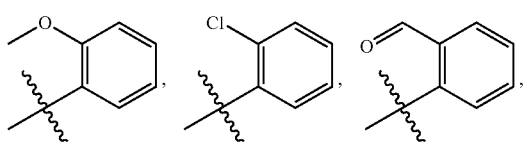,

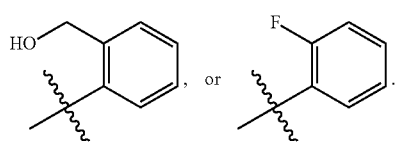, or 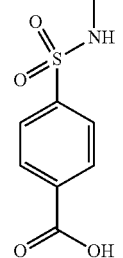.

30. An aqueous composition, comprising the macrocyclic compound of claim 1 in an anionic form.

31. An aqueous composition, comprising the macrocyclic compound of claim 25 in an anionic form.

32. The aqueous composition of claim 31, wherein the anionic form of the macrocyclic compound has a structure

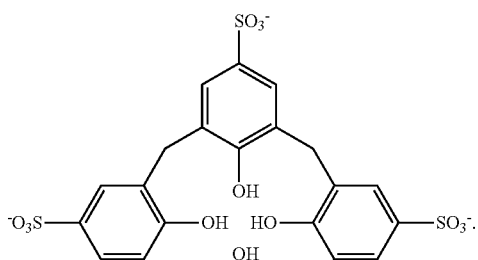

33. The array of claim 26, wherein the anionic form of the macrocyclic compound in the aqueous environment has a structure

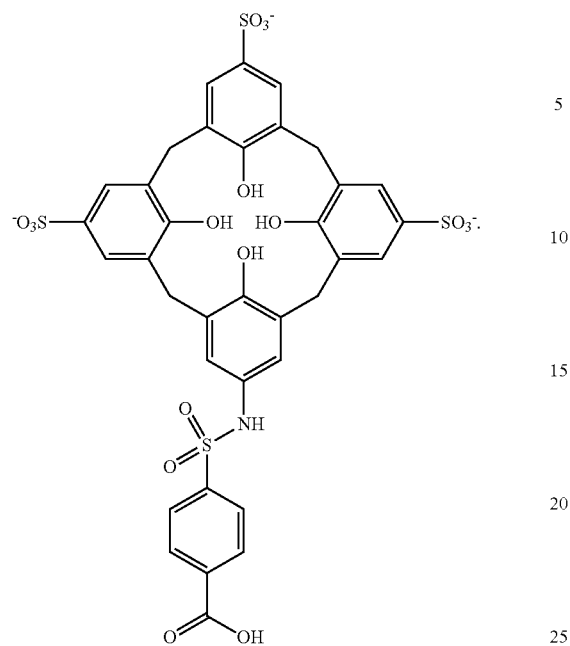
* * * * *